United States Patent
Kealey et al.

(10) Patent No.: US 11,020,254 B2
(45) Date of Patent: Jun. 1, 2021

(54) THIN-FILM MICROMESH COVERS FOR MEDICAL DEVICES AND RELATED METHODS

(71) Applicant: NSVascular, Inc., Los Angeles, CA (US)

(72) Inventors: Colin Kealey, Los Angeles, CA (US); Ian A. Cook, Los Angeles, CA (US); Vikas Gupta, Los Angeles, CA (US)

(73) Assignee: Monarch Biosciences, Inc., Los Angeles, CA (US)

( * ) Notice: Subject to any disclaimer, the term of this patent is extended or adjusted under 35 U.S.C. 154(b) by 211 days.

(21) Appl. No.: 15/849,469

(22) Filed: Dec. 20, 2017

(65) Prior Publication Data

US 2018/0110637 A1    Apr. 26, 2018

Related U.S. Application Data

(63) Continuation of application No. PCT/US2016/039436, filed on Jun. 24, 2016.
(Continued)

(51) Int. Cl.
*A61F 2/91* (2013.01)
*A61F 2/90* (2013.01)
(Continued)

(52) U.S. Cl.
CPC .................. *A61F 2/91* (2013.01); *A61F 2/90* (2013.01); *A61L 27/04* (2013.01); *A61L 27/06* (2013.01);
(Continued)

(58) Field of Classification Search
None
See application file for complete search history.

(56) References Cited

U.S. PATENT DOCUMENTS

| 6,312,463 B1 | 11/2001 | Rourke et al. |
| 6,666,882 B1 | 12/2003 | Bose et al. |

(Continued)

FOREIGN PATENT DOCUMENTS

| WO | WO 2011/150118 | 12/2011 |
| WO | WO 2014/131037 | 8/2014 |

(Continued)

OTHER PUBLICATIONS

PCT International Search Report and Written Opinion of International Application No. PCT/US2016/039436, 12 pages, dated Sep. 16, 2016.

(Continued)

*Primary Examiner* — Jiong-Ping Lu
(74) *Attorney, Agent, or Firm* — Haynes and Boone, LLP

(57) ABSTRACT

A thin-film covered stent device may include a thin-film mesh and a stent backbone covered by the thin-film mesh, thereby forming a dual-layer stent structure. The thin-film covered stent device may have smaller pores and a high pore density compared to conventional stents. For example, the thin-film covered stent device may have a slit length of between 50 and 250 micrometers and a pore density of between 134 and 227 pores per mm$^2$. The thin-film covered stent device facilitates rapid healing of tissue defects such as those encountered during the endovascular treatment of an aneurysm.

6 Claims, 22 Drawing Sheets

Related U.S. Application Data

(60) Provisional application No. 62/185,513, filed on Jun. 26, 2015, provisional application No. 62/188,218, filed on Jul. 2, 2015, provisional application No. 62/209,185, filed on Aug. 24, 2015, provisional application No. 62/209,254, filed on Aug. 24, 2015, provisional application No. 62/216,965, filed on Sep. 10, 2015.

(51) Int. Cl.
　　*A61L 27/06*　　(2006.01)
　　*A61L 31/02*　　(2006.01)
　　*A61L 27/04*　　(2006.01)
　　*A61L 31/00*　　(2006.01)
　　*C23C 14/04*　　(2006.01)
　　*A61F 2/82*　　(2013.01)

(52) U.S. Cl.
　　CPC .............. *A61L 31/00* (2013.01); *A61L 31/022* (2013.01); *C23C 14/04* (2013.01); *C23C 14/042* (2013.01); *A61F 2002/823* (2013.01); *A61F 2002/825* (2013.01); *A61F 2210/0004* (2013.01); *A61F 2210/0014* (2013.01); *A61F 2230/0017* (2013.01); *A61F 2240/001* (2013.01); *A61F 2240/004* (2013.01); *A61F 2250/0023* (2013.01); *A61F 2250/0031* (2013.01); *A61F 2250/0067* (2013.01)

(56) References Cited

U.S. PATENT DOCUMENTS

| | | |
|---|---|---|
| 6,746,890 B2 | 6/2004 | Gupta et al. |
| 7,311,727 B2 | 12/2007 | Mazumder et al. |
| 2005/0070989 A1 | 3/2005 | Lye et al. |
| 2005/0186241 A1 | 8/2005 | Boyle et al. |
| 2007/0173787 A1* | 7/2007 | Huang ............... A61F 2/82 604/891.1 |
| 2007/0276469 A1* | 11/2007 | Tenne .............. A61B 17/12022 623/1.38 |
| 2008/0004653 A1 | 1/2008 | Sherman et al. |
| 2012/0245706 A1 | 9/2012 | Alavi et al. |
| 2017/0265870 A1 | 9/2017 | Kealey et al. |

FOREIGN PATENT DOCUMENTS

| | | | |
|---|---|---|---|
| WO | WO 2015/061496 | 4/2015 | |
| WO | WO2015061496 | * 4/2015 | ............ A61F 2/82 |
| WO | WO 2016/168765 | 10/2016 | |
| WO | WO 2016/210380 | 12/2016 | |

OTHER PUBLICATIONS

PCT International Search Report and Written Opinion of International Application No. PCT/US2016/040864, 12 pages, dated Nov. 29, 2016.

Holger Gerullis et al., "Coating with Autologous Plasma Improves Biocompatibility of Mesh Grafts In Vitro: Development Stage of a Surgical Innovation", BioMed Research International, vol. 2013, Jan. 1, 2013 (Jan. 1, 2013), pp. 1-6.

* cited by examiner

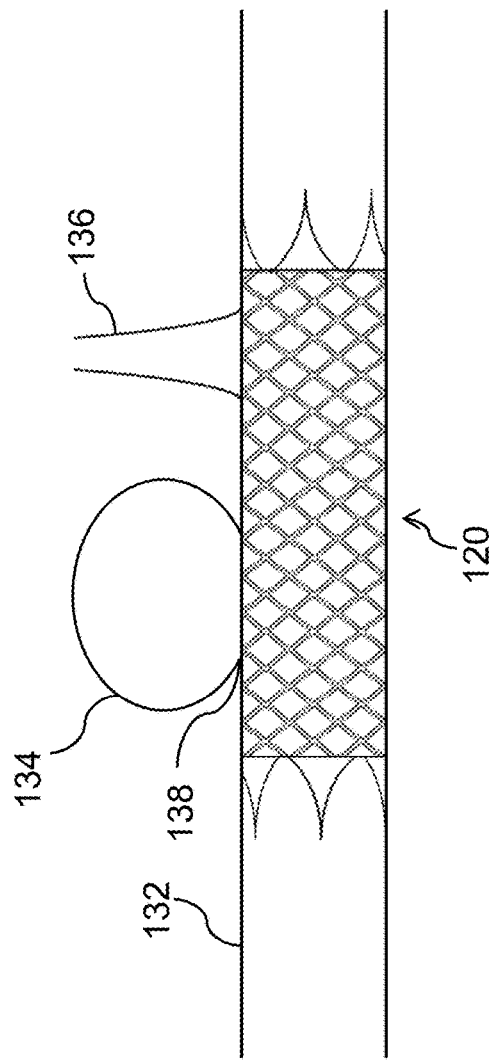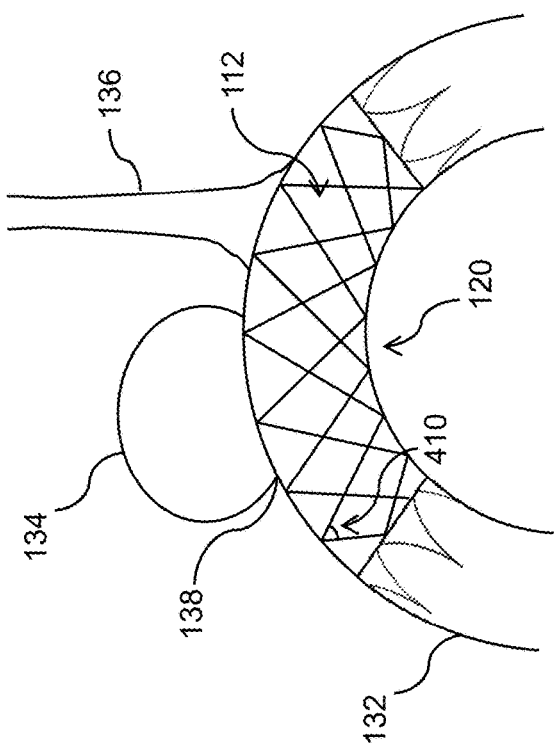
FIG. 4A
FIG. 4B

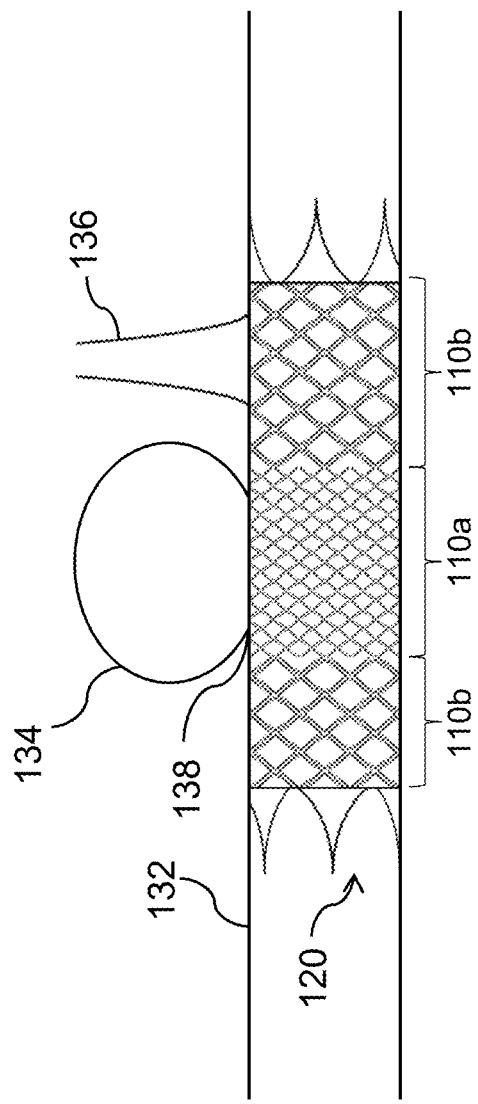

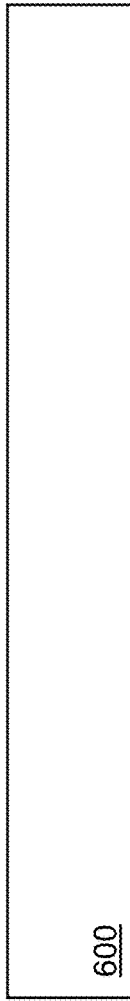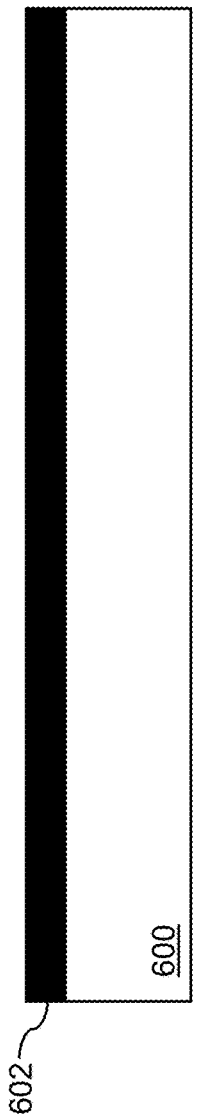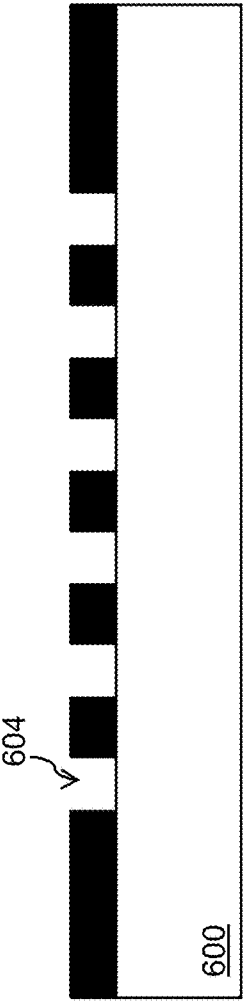

THIN-FILM MICROMESH COVERS FOR MEDICAL DEVICES AND RELATED METHODS

CROSS-REFERENCE TO RELATED APPLICATIONS

The present application is a continuation of International Application No. PCT/US2016/039436, filed on Jun. 24, 2016, which claims the benefit of U.S. Provisional Application No. 62/185,513, filed on Jun. 26, 2015, U.S. Provisional Application No. 62/188,218, filed on Jul. 2, 2015, U.S. Provisional Application No. 62/209,185, filed on Aug. 24, 2015, U.S. Provisional Application No. 62/209,254, filed on Aug. 24, 2015, and U.S. Provisional Application No. 62/216,965, filed on Sep. 10, 2015, which are all hereby incorporated by reference in their entirety.

TECHNICAL FIELD

The present disclosure generally relates to medical devices and, more particularly, to thin-film micromesh covers for medical devices and related methods.

BACKGROUND

Tissue defects involve an absence of healthy tissue in a body area where such tissue would normally be present. For example, a common tissue defect includes arterial or venous aneurysms, in which there is a defect in a blood vessel wall that causes an outpouching of the vessel tissue. Other common tissue defects include arteriovenous fistulas, intestinal fistulas, colonic fistulas, anal fistulas, hernias, and traumatic wounds.

Covered stents are used throughout the body to treat a variety of tissue defects. These devices may be composed of a stent backbone that provides structural support and a cover that limits, or completely eliminates, the porosity of the covered stent. The purpose of the cover is to provide a barrier that limits the flow of fluid, particulates, or tissue in-growth through the covered stent following placement at a tissue defect site, such as a blood vessel with an aneurysm.

Covered stents have been used to treat aneurysms in disparate locations, such as the aorta, iliac arteries, renal arteries, popliteal arteries, splenic arteries, femoral arteries, tibial arteries, and throughout the neurovasculature. Covered stents can also be used for other applications where there is a desire to limit emboli from the blood vessel wall following device placement. For example, covered stents may be used for treating carotid atherosclerosis where emboli from atherosclerotic plaque can dislodge following stenting and then travel into the brain, potentially causing ischemic stroke. In another example, covered stents may be used for treating occluded coronary artery bypass grafts where emboli can dislodge from the atherosclerotic plaque following stenting, potentially leading to myocardial infarction. Covered stents are also used as a primary treatment for atherosclerosis in certain vascular beds, such as the peripheral vasculature, where the covering is thought to act as a barrier for the propagation and enlargement of atherosclerotic plaque.

BRIEF DESCRIPTION OF THE DRAWINGS

FIG. 4A is a diagrammatic cross-sectional view of a blood vessel in which a thin-film covered stent is placed according to an embodiment.

FIG. 4B is a diagrammatic cross-sectional view of a curved blood vessel in which a thin-film covered stent is placed according to an embodiment.

FIG. 4C is a diagrammatic cross-sectional view of a blood vessel in which a thin-film covered stent with a variable porosity is placed according to an embodiment.

Figure 1:
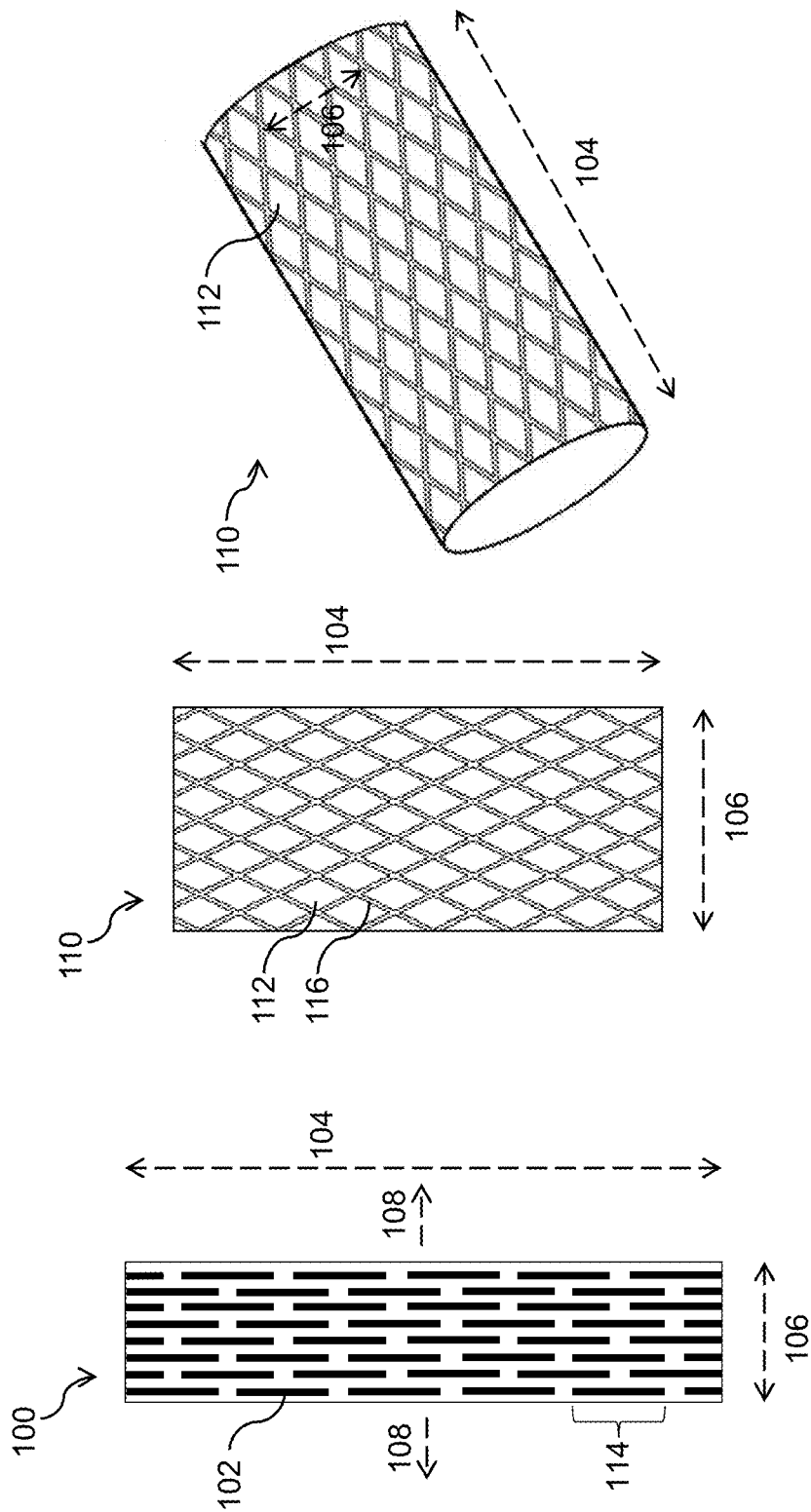
FIG. 1A is a diagrammatic top plan view of a thin-film mesh that expands radially prior to expansion according to an embodiment.
FIG. 1B is a diagrammatic top plan view of the thin-film mesh of FIG. 1A after expansion.
FIG. 1C is a diagrammatic perspective view of the thin-film mesh of FIG. 1A after expansion.

Embodiments of the present disclosure and their advantages are best understood by referring to the detailed description that follows. It should be appreciated that like reference numerals are used to identify like elements illustrated in one or more of the figures, in which the showings therein are for purposes of illustrating the embodiments and not for purposes of limiting them.

DETAILED DESCRIPTION

Thin-film micromeshes for medical devices and related methods are provided. A thin-film micromesh (also referred to as a microporous thin-film mesh or a thin-film mesh) is composed of a metallic material or a pseudometallic material. For example, the thin-film mesh may be a thin-film Nitinol (TFN) mesh composed of Nitinol (i.e. Nickel Titanium).

A thin-film mesh composed of metallic material provides a number of advantages compared to a thin-film mesh composed of polymeric material, which is commonly used for covered stent grafts, hernia repair, and fistulae. Thin-film meshes composed of metallic material facilitate more robust cellular adhesion and tissue incorporation compared to thin-film meshes composed of polymeric material. Further, thin-film meshes composed of metallic material may be superior for long term implants because implantation of polymeric biomaterials tends to elicit a greater inflammatory response than metallic biomaterials.

The thin-film mesh may be formed using deposition techniques and micropatterned silicon wafers such that the composition, thickness, and pattern of the thin-film mesh are controlled at the micrometer and/or nanometer level. The thin-film mesh may be formed by sputter deposition of Nitinol onto a silicon wafer patterned using deep reactive ion etching (DRIE). The silicon wafer is patterned with a series of slits such that corresponding slits formed on a thin-film mesh have a long dimension that is significantly greater than the width of the struts. This allows for a fabricated thin-film mesh that is capable of significant expansion in the order of 50% to 800% from its original fabricated length. Once expanded, the slits of the thin-film mesh assume a diamond-shaped pore configuration. The dimensions of the diamond-shaped pores can be precisely controlled during fabrication and expansion of the thin-film mesh such that the diamond-shaped pores have dimensions that facilitate healing of a tissue defect. During fabrication and expansion, features such as the percent metal coverage (i.e., the percentage of surface area covered by the thin-film mesh, or 100%—porosity in percentage), the pore density (i.e., the number of pores per $mm^2$ of surface area), edge density (i.e. total length of pore edges per $mm^2$ of surface area), and pore geometry may be determined. The thin-film mesh may be used as a stand-alone device or may be combined with other medical devices such as endovascular stents to create a covered stent. The covered stent may be used, for example, for treating aneurysms throughout the body or for carotid stenting.

FIG. 1A is a diagrammatic top plan view of a thin-film mesh 100 that expands radially prior to expansion. Thin-film mesh 100 has a series of micropatterned slits 102, also referred to as closed fenestrations. Thin-film mesh 100 has a long axis 104 and a short axis 106. Slits 102 are oriented parallel or substantially parallel (e.g., oriented at an angle between 0 degrees and 30 degrees) to axis 104, also referred to as the slit axis 104. Accordingly, slits 102 are oriented perpendicular or substantially perpendicular (e.g., oriented at an angle between 60 degrees and 90 degrees) to axis 106. Thin-film mesh 100 may be expanded by extending thin-film mesh 100 in directions 108 along axis 106, also referred to as the axis of expansion 106, to form an expanded thin-film mesh 110 of FIGS. 1B-C, in which slits 102 have opened up to form a series of diamond-shaped pores 112.

Each of slits 102 may have slit length 114 (length along axis 104) of between 50 and 500 μm (micrometers, or microns). Slit length 114 may be modulated based on the type of medical treatment, the body region being treated, and/or the type of aneurysm being treated.

Thin-film mesh 100/110 fabricated with slit length 114 of between 50 μm and 250 μm provides advantageous reconstruction of tissue defects that are superior to other slit lengths. Thin-film mesh 100/110 fabricated with slit length 114 of between 50 μm and 250 μm promotes rapid fibrin deposition and cell growth (e.g., endothelialization) when placed in a blood vessel.

The ability of thin-film mesh 100/110 to effectively expand along axis 106 may depend on the length of slits 102. Slits 102 with a longer slit length 114 will result in thin-film mesh 100/110 with increased ability for expansion, while slits 102 with a shorter slit length 114 will result in thin-film mesh 100/110 with a decreased ability for expansion.

In some embodiments, thin-film mesh 100 is fabricated as two layers of thin-film on a silicon wafer using silicon wafer micromachining technology, as described below in relation to FIGS. 5, 6A-Q, and 7A-H. As the two layers of thin-film are stacked, only the top layer is visible in FIG. 1A, and the two layers of thin-film may be joined at the two edges along axis 104.

FIG. 1B is a diagrammatic top plan view of thin-film mesh 110 formed by expanding thin-film mesh 100 of FIG. 1A. Thin-film mesh 110 forms a plurality of diamond-shaped pores 112, also referred to as open fenestrations. The expansion may extend thin-film mesh 100 along axis 106 such that there is a large increase in width (length along axis 106) but a small decrease in longitudinal length (length along axis 104). In some embodiments, the expansion may extend thin-film mesh 100 along axis 104 in a range from 25% to 800%.

When thin-film mesh 100 of FIG. 1A is expanded to thin-film mesh 110, slits 102 of thin-film mesh 100 open up into pores/fenestrations 112 to form a "chain-link" fence pattern, such as diamond-shaped pores/fenestrations. Thin-film mesh 110 forms struts 116 around each diamond-shaped pore/fenestration 112. It will be appreciated that other pore/fenestration shapes may be used in alternative embodiments. The diamond shape of each pore 112 is longer along axis 104, also referred to as long diagonal axis 104 of diamond-shaped pore 112, and shorter along axis 106, also referred to as the short diagonal axis 106 of diamond-shaped pore 112.

Figure 3:
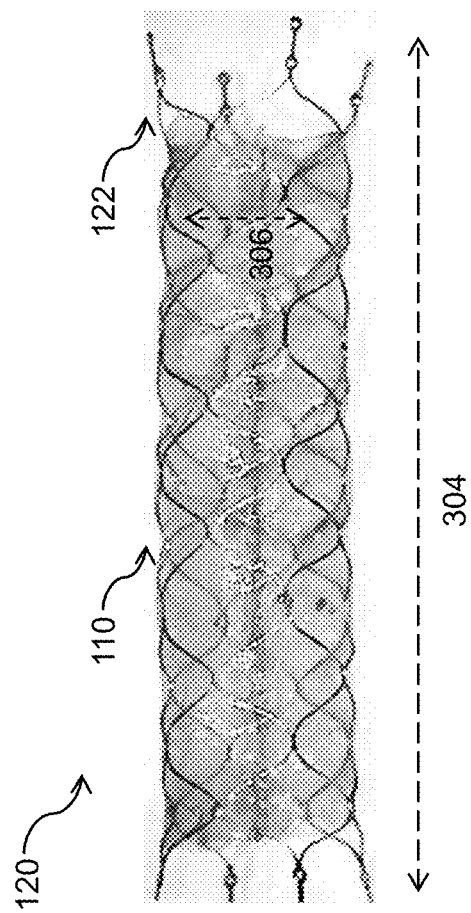
FIG. 3 is an image of a side elevational view of a thin-film covered stent according to an embodiment.

FIG. 1C is a diagrammatic perspective view of thin-film mesh 110 formed by expanding thin-film mesh 100 of FIG. 1A. As shown in FIG. 1C, thin-film mesh 110 has a three-dimensional form. In some embodiments, thin-film mesh 100 is fabricated as two layers of thin-film joined at two longitudinal edges along axis 104, and may be expanded to thin-film mesh 110 forming a cylindrical tube. In some embodiments, thin-film mesh 100 is fabricated as two layers of thin-film joined at two longitudinal edges along axis 104 and a bonding metal is deposited at the longitudinal edge between the two layers such that heating of the construct to the bonding metal's melting temperature results in fusion of the two layers to form a seam. Cylindrical thin-film mesh 110 may be used, for example, as a thin-film mesh cover for a stent backbone, as shown in FIG. 3.

Thin-film mesh 100/110 fabricated with slit length 114 of between 50 μm and 500 μm may have a pore density of between 15 pores/$mm^2$ and 2217 pores/$mm^2$ and a percent metal coverage (PMC) of between 6% and 83%. The pore density and the percent metal coverage may be modulated based on the type of medical treatment, the body region being treated, and/or the type of aneurysm being treated.

Thin-film mesh 100/110 fabricated with slit length 114 of between 50 μm and 200 μm may have a high pore density of between 81 pores/$mm^2$ and 1075 pores/$mm^2$ and a low percent metal coverage of between 19% and 66% that provides advantageous reconstruction of tissue defects that are superior to other pore densities and percent metal coverages. Thin-film mesh 100/110 with a pore density of between 81 pores/mm² and 1075 pores/mm² and a percent metal coverage of between 19% and 66% advantageously promotes a planar deposition of fibrin followed by rapid cell growth (e.g., endothelialization) when placed in a blood vessel.

Figure 2:
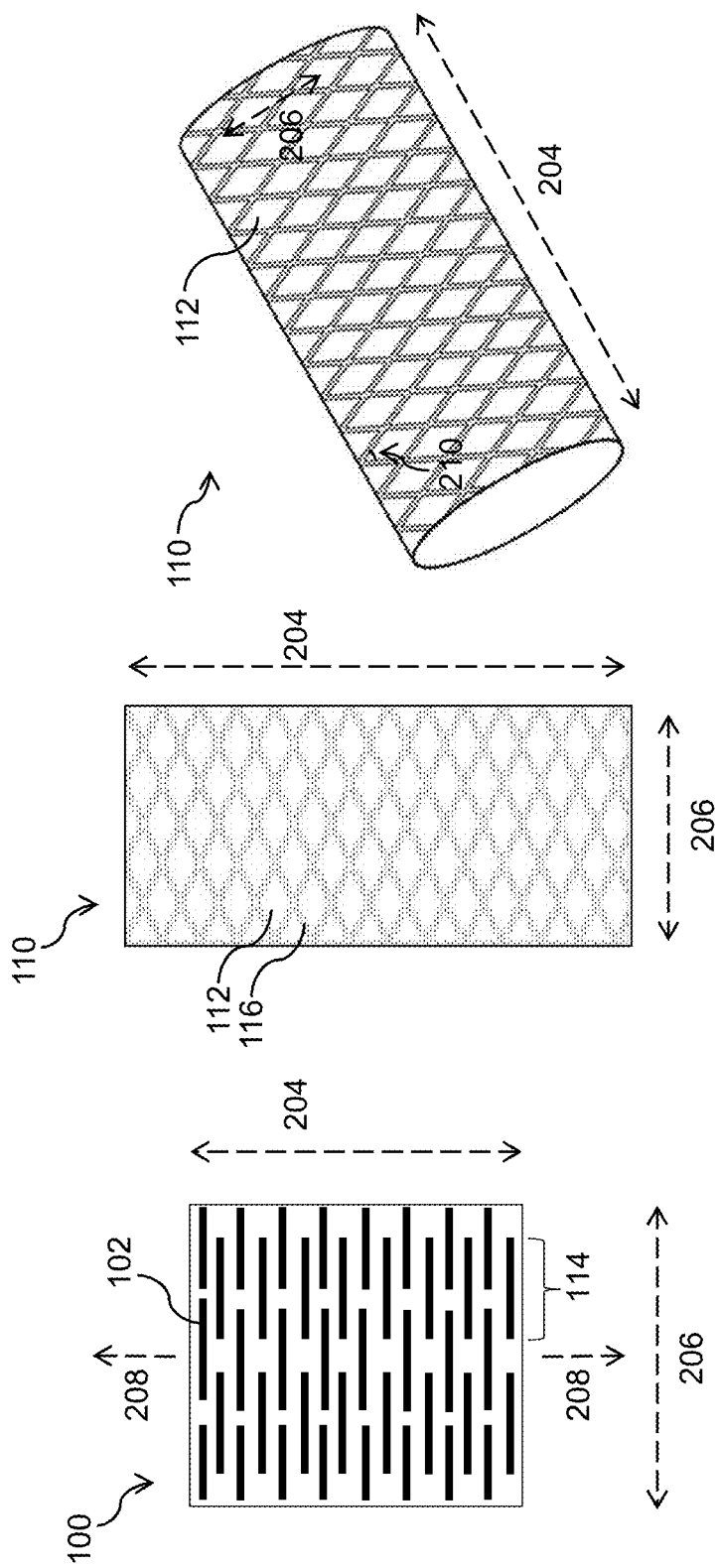
FIG. 2A is a diagrammatic top plan view of a thin-film mesh that expands longitudinally prior to expansion according to an embodiment.
FIG. 2B is a diagrammatic top plan view of the thin-film mesh of FIG. 2A after expansion.
FIG. 2C is a diagrammatic perspective view of the thin-film mesh of FIG. 2A after expansion.

FIG. 2A is a diagrammatic top plan view of thin-film mesh 100 that expands longitudinally prior to expansion. Thin-film mesh 100 has a series of micropatterned slits 102, also referred to as closed fenestrations. Thin-film mesh 100 has a long axis 204 and a short axis 206. Slits 102 are oriented parallel or substantially parallel (e.g., oriented at an angle between 0 degrees and 30 degrees) to axis 206, also referred to as the slit axis 206. Accordingly, slits 102 are oriented perpendicular or substantially perpendicular (e.g., oriented at an angle between 90 degrees and 60 degrees) to axis 204. Thin-film mesh 100 may be expanded by extending thin-film mesh 100 in directions 208 along axis 204, also referred to as the axis of expansion 204, to form an expanded thin-film mesh 110 of FIGS. 2B-C, in which slits 102 have opened up to form a series of diamond-shaped pores 112, also referred to as open fenestrations.

Each of slits 102 may have slit length 114 (length along axis 206) of between 50 μm and 500 μm. Slit length 114 may be modulated based on the type of medical treatment, the body region being treated, and/or the type of aneurysm being treated.

Thin-film mesh 100/110 fabricated with slit length 114 of between 50 μm and 250 μm provides advantageous reconstruction of tissue defects that are superior to other slit lengths. Thin-film mesh 100/110 fabricated with slit length 114 of between 50 μm and 250 μm promotes rapid fibrin deposition and cell growth (e.g., endothelialization) when placed in a blood vessel.

The ability of thin-film mesh 100/110 to effectively expand along axis 204 may depend on the length of slits 102. Slits 102 with a longer slit length 114 will result in thin-film mesh 100/110 with increased ability for expansion, while slits 102 with a shorter slit length 114 will result in thin-film mesh 100/110 with a decreased ability for expansion.

In some embodiments, thin-film mesh 100 is fabricated as two layers of thin-film on a silicon wafer using silicon wafer micromachining technology, as described below in relation to FIGS. 5, 6A-Q, and 7A-H. As the two layers of thin-film are stacked, only the top layer is visible in FIG. 2A, and the two layers of thin-film may be joined at the two edges along axis 204. In some embodiments, the two layers may have a bonding metal in between to facilitate fusion of the two layers when the bonding metal is heated to its melting temperature.

Each of the two layers of thin-film mesh 100 may have a width (length along axis 206) that is approximately half of the circumference of the final device, such as thin-film mesh 110 expanded to its three-dimensional form (e.g., a cylindrical tube) as shown in FIG. 2C. The term "approximately," as used herein when referring to a measurable value is meant to encompass variations of ±20%, ±10%, ±5%, ±1%, ±0.5%, or ±0.1% of the value. Accordingly, cylindrical thin-film mesh 110 may have a circumference that is approximately twice or slightly less than twice of the width of thin-film mesh 100. For example, if thin-film mesh 100 is 4 mm wide, cylindrical thin-film mesh 110 may have a circumference of 7.4 mm and a diameter of 2.4 mm.

FIG. 2B is a diagrammatic top plan view of thin-film mesh 110 formed by expanding thin-film mesh 100 of FIG. 2A. Thin-film mesh 110 forms a plurality of diamond-shaped pores 112 (e.g., open fenestrations). The expansion may extend thin-film mesh 100 along axis 204 such that there is a large increase in longitudinal length (length along axis 204) but a small decrease in width (length along axis 206). In some embodiments, the expansion may longitudinally extend thin-film mesh 100 along axis 204 in a range from 25% to 800%.

When thin-film mesh 100 of FIG. 2A is expanded to thin-film mesh 110, slits 102 of thin-film mesh 100 open up into pores/fenestrations 112 to form a "chain-link" fence pattern, such as diamond-shaped pores/fenestrations. Thin-film mesh 110 forms struts 116 around each diamond-shaped pore/fenestration 112. It will be appreciated that other pore/fenestration shapes may be used in alternative embodiments. The diamond shape of each pore 112 may be longer along axis 206, also referred to as long diagonal axis 206 of diamond-shaped pore 112, and shorter along axis 204, also referred to as the short diagonal axis 204 of diamond-shaped pore 112.

FIG. 2C is a diagrammatic perspective view of thin-film mesh 110 formed by expanding thin-film mesh 100 of FIG. 2A. As shown in FIG. 1C, thin-film mesh 110 has a three-dimensional form. In some embodiments, thin-film mesh 100 is fabricated as two layers of thin-film joined at two longitudinal edges along axis 204, and may be expanded to thin-film mesh 110 forming a cylindrical tube. Cylindrical thin-film mesh 110 may be used, for example, as a thin-film mesh cover for a stent backbone, as shown in FIG. 3.

Thin-film mesh 100/110 fabricated with slit length 114 of between 50 μm and 500 μm may have a pore density of between 15 pores/mm² and 2217 pores/mm² and a percent metal coverage (PMC) of between 6% and 83%. The pore density and the percent metal coverage may be modulated based on the type of medical treatment, the body region being treated, and/or the type of aneurysm being treated.

Thin-film mesh 100/110 fabricated with slit length 114 of between 50 μm and 20 μm may have a high pore density of between 81 pores/mm² and 1075 pores/mm² and a low percent metal coverage of between 19% and 66% that provides advantageous reconstruction of tissue defects that are superior to other pore densities and percent metal coverages. Thin-film mesh 100/110 with a pore density of between 81 pores/mm² and 1075 pores/mm² and a percent metal coverage of between 19% and 66% advantageously promotes a planar deposition of fibrin followed by rapid cell growth (e.g., endothelialization) when placed in a blood vessel.

The orientation of slits 102 in FIG. 2A also provides advantages to thin-film mesh 100/110 when used as a stent cover for a thin-film covered stent. Prior to expansion, thin-film mesh 100 includes slits 102 oriented perpendicular or substantially perpendicular (e.g., oriented at an angle between 90 degrees and 60 degrees) to long axis 204 of thin-film mesh 100. After expansion along axis of expansion 204, thin-film mesh 110 includes diamond-shaped pores 112 oriented such that long diagonal axis 206 of diamond-shaped pores 112 are perpendicular to, or substantially perpendicular to, long axis 204 of thin-film mesh 110. Accordingly, thin-film mesh 100/110 advantageously provides vastly improved longitudinal flexibility and expandability compared to conventional covered stents. Further, a thin-film covered stent that includes thin-film mesh 100/110 advantageously provides vastly improved flexibility to bend, arc, and/or loop around curves compared to conventional covered stent.

FIG. 3 is an image of a side elevational view of a thin-film covered stent 120. Thin-film covered stent 120 includes thin-film mesh 110, such as thin-film mesh 110 of FIGS.

1B-C or FIGS. 2B-C, and a stent backbone 122. Stent backbone 122 may be an elastic and self-expanding stent backbone. Stent backbone 122 may be flared at one or both its distal end to facilitate placement at a blood vessel. Thin-film mesh 110 expanded to its three-dimensional form (e.g., a cylindrical tube) is assembled on stent backbone 122, which provides structural support for thin-film mesh 110 while maintaining the advantageous features of thin-film mesh 110, such as rapid fibrin deposition and cell growth (e.g., endothelialization) when placed in a blood vessel. Thin-film mesh 110 may be oriented such that long axis 104/204 of thin-film mesh 110 is parallel to, or substantially parallel to, long/longitudinal axis 304 of thin-film covered stent 120/stent backbone 122.

In some embodiments, thin-film mesh 110 of FIGS. 2B-C is placed on stent backbone 122 such that long diagonal axis 206 of diamond-shaped pores 112 are perpendicular to, or substantially perpendicular to, long axis 304 of thin-film covered stent 120/stent backbone 122. As thin-film mesh 110 of FIGS. 2B-C has extreme longitudinal expandability and can be flexibly bent around curves, thin-film covered stent 120 provides vastly improved flexibility to bend, arc, and/or loop around curves, such as curves in blood vessels.

Thin-film mesh 110 may be placed over stent backbone 122 such that thin-film mesh 110 wraps around stent backbone 122. Alternatively, thin-film mesh 110 may be attached to the interior surface of stent backbone 122. Thin-film mesh 110 may include one or more attachment points or areas that are used to attach thin-film mesh 110 to stent backbone 122. Radiopaque marker may be used at the attachment points to attach thin-film mesh 110 to stent backbone 122, which advantageously assists in visualizing the position of thin-film covered stent 120 during and after implantation.

In some embodiments, stent backbone 122 is a wire stent backbone composed of a superelastic alloy such as Nitinol. Stent backbone 122 may be formed by laser cutting a hypotube of superelastic alloy.

In other embodiments, stent backbone 122 is a bioabsorbable stent composed of a bioabsorbable metal or polymeric material that is absorbed, degraded, dissolved, or otherwise fully broken down after a predetermined amount of time (e.g., 3-6 months, 6-24 months, etc.) after implantation in a patient while thin-film mesh 110 remains in the patient. The thin-film covered bioabsorbable stent device may have advantages over conventional covered stents that use a stent backbone or scaffold that is not absorbed or does not degrade, which presents potential dangers and risks. For example, long-term presence of a stent backbone is potentially dangerous because it could serve as a continuing risk for thrombotic complications. Further, the stent backbone may exert a mechanical force on the parent artery that changes its compliance and flexibility in a manner that may also increase the likelihood of parent artery stenosis. Advantageously, thin-film covered bioabsorbable stent device delivers the thin-film mesh to the target site of vascular pathology such as an aneurysms or arterial disease while the bioabsorbable stent backbone degrades or is absorbed. For example, the bioabsorbable stent backbone may provide structural support for thin-film mesh 110 while maintaining the advantageous features of thin-film mesh 110, such as fibrin deposition and cell growth (e.g., endothelialization) when placed in a blood vessel. By the time the bioabsorbable stent degrades, the blood vessel may have fully healed and no longer require the mechanical support provided by the bioabsorbable stent backbone. In another example, the bioabsorbable stent backbone may simply be a means to deliver thin-film mesh 110 to an aneurysm neck region and not play a major role in aneurysm occlusion and healing of the aneurysm neck region.

It will be appreciated that stent backbone 122 may include other material or structure in alternative embodiments. Moreover, it will be appreciated that thin-film mesh 110 may be attached to other medical devices that would benefit from fibrin deposition and cell growth in further embodiments.

One skilled in the art will appreciate that thin-film covered stent 120 may be configured or modified based on the type of vascular pathology being treated. For example, thin-film covered stent 120 may be used to treat atherosclerotic plaque throughout the body by implanting the device at a target vessel to open the vessel and reestablish blood flow, followed by facilitating rapid healing of the vessel and isolation of the atherosclerotic plaque. Further, the thin-film meshes may be configured or modified to improve their biological interaction with a vessel wall and thereby facilitate the desired healing response. Further, thin-film covered stent 120 may have uses for non-vascular applications. For example, fistulas, which are pathological orifices between two body organs or a body organ and the outside body surface, could be treated with a thin-film covered stent 120 where thin-film mesh 110 facilitates healing of the fistula and closure of the unwanted orifice. Additionally, thin-film covered stent 120 could be used to treat stenosis throughout the body (e.g., esophageal, renal, urinary, biliary, tracheobronchial, or gastrointestinal stenosis).

In some embodiments, thin-film mesh 110 of thin-film covered stent 120 is a thin-film covered carotid stent configured to be placed in the internal carotid artery distal to the carotid bifurcation. Thin-film mesh 110 has pores 112 that are small enough to prevent distal embolization of clinically relevant particles that may lead to ischemic strokes. Clinically-relevant microembolus particles less than 240 μm in diameter are less likely to lead to clinically relevant ischemic events. Additionally, as the size of a microembolus decreases, the patient's ability to lyse and degrade the particle using endogenous enzymes will increase. Accordingly, the thin-film mesh includes pores with a largest dimension that is 240 μm or less. This value could be substantially less than 240 μm (e.g., 100 μm or less or 50 μm or less) depending on the technology used to fabricate the thin-film mesh. This can lead to a high pore density (e.g., approximately 2000 pores/mm$^2$). It should be appreciated that as the pore density of the device is increased, the size of the corresponding micro-emboli that can fit through the pores will decrease. It should also be appreciated that thin-film mesh 110 can be composed of any of a number of materials including a thin-film shape memory alloy (e.g., Nitinol), polytetrafluoroethylene (PTFE), or polyethylene terephthalate (Dacron). Thin-film mesh 110 may be used as a vehicle for drug delivery and coated with a drug eluting polymer that reduces the rate of neointimal hyperplasia or increases the biocompatibility or hemocompatibility of thin-film covered stent 120.

FIG. 4A is a diagrammatic cross-sectional view of a blood vessel 132 in which thin-film covered stent 120 is inserted. An aneurysm 134 is localized at blood vessel 132, and blood vessel 132 is connected to a branch vessel 136 (e.g., a branch artery or vein).

Thin-film covered stent 120 includes significant advancements over conventional flow diverter stents. Thin-film covered stent 120 advantageously diverts blood flow into the aneurysm and promotes rapid deposition of fibrin and endothelialization at the neck 138 of aneurysm 134 so that aneurysm 134 is occluded, while at the same time allowing blood flow through branch vessel 136. Thin-film covered stent 120 thus strikes the balance between diverting flow from aneurysm sac 134 while permitting flow in perianeurysmal branch vessels 136.

Thin-film covered stent 120 advantageously has a reduced rate of delayed aneurysm rupture when compared to conventional flow diverter stents. Conventional wire flow diverter stents may provide occlusion of aneurysm necks, but because the pores of such devices are often filled with particles made up of blood coagulation products, inflammatory cells, and cellular debris, such particles may be dislodged and thereby allow a sudden increase in blood flow into the sac, causing delayed aneurysm rupture. Indeed, endothelialization is slow to occur and is often partial at best in conventional wire flow diverter stents. In contrast, thin-film mesh 110 provides a structure on which the blood vessel walls are rapidly rebuilt through endothelialization, promoting a healthy and stable cellular lining. Further, the rate of delayed aneurysm rupture is significantly reduced because the cellular lining is not prone to dislodging of particles such as blood coagulation products and other particles.

Also, thin-film covered stent 120 advantageously allows use of a smaller delivery catheter. Thin-film covered stent 120 uses thin-film mesh 110 with a thickness of between 1 micron and 50 microns as a covering, which has the advantage of adding very little bulk to stent backbone 122 and, thereby, allowing thin-film covered stent 120 to be packaged and delivered via a very small catheter.

FIG. 4B is a diagrammatic cross-sectional view of a curved blood vessel 132 in which thin-film covered stent 120 is inserted. Aneurysm 134 is localized at a tortuous bend of blood vessel 132, and blood vessel 132 is connected to branch vessel 136 (e.g., a branch artery or vein).

Thin-film covered stent 120 advantageously provide vastly improved flexibility to bend, arc, and/or loop around curves, such as curves in tortuous vascular beds. A significant problem with conventional covered stents is their tendency to kink and failing to achieve good wall apposition when placed in tortuous vascular beds. This tendency is the result of competing stent device demands. First, the stent device must be delivered from a small catheter and expand to a much larger radius. Therefore, flexible, stretchable materials are often used for stent coverings. One of the most commonly used materials is expandable polytetrafluoroethylene (ePTFE). The difficulty comes when the covering material is compressed into a small diameter (e.g., in the order of millimeters) to fit into a delivery catheter and subsequently expands to a much larger diameter (e.g., in the order of centimeters). This stretches the covering substantially in the radial direction and thereby limits the stent device's ability to stretch in the longitudinal direction. Such a situation can lead to kinking and poor wall apposition of the device, which, in turn, can lead to undesirable outcomes such as poor aneurysm occlusion or device protrusion in to the vessel lumen. As thin-film covered stent 120 may flexibility bend, arc, and/or loop around curves, thin-film covered stent 120 provides a high-density thin film mesh 110 covering that can limit the flow of fluid or particulates while still achieving excellent wall apposition and no device kinking even in highly tortuous vascular beds.

As can be seen in FIG. 4B, when thin-film covered stent 120 is placed around the tortuous bend of vessel 132, the portion of thin-film mesh 110 facing the outer radius of the curve stretches to conform to the outer radius of the curve. This allows thin-film covered stent 120 to achieve full radial expansion and good wall apposition, even in highly tortuous anatomy.

In some embodiments, thin-film covered stent 120 utilizes thin-film mesh 100/110 that expands longitudinally as shown in FIGS. 2A-C, which confers further kink-resistant advantages due to the axis of expansion 204 being parallel to the long/longitudinal axis 304 of thin-film covered stent 120. When thin-film covered stent 120 is in its straight state, diamond-shaped pore/fenestration 112 may have an angle $\theta_1$ 210, as shown in FIG. 2C. When thin-film covered stent 120 is in its curved state to conform to a curved blood vessel, as shown in FIG. 4B, diamond-shaped pore/fenestration 112 on the outer radius of the curve may have an angle $\theta_2$ 410 that is larger than angle $\theta_1$ 210 because diamond-shaped pores/fenestrations 112 on the outer radius have further expanded laterally.

Moreover, thin-film covered stent 120 may use stent backbone 122 with less radial force if longitudinally expanding thin-film mesh 100/110 of FIGS. 2A-C is used as compared to radially expanding thin-film mesh 100/110 of FIGS. 1A-C. Thin-film covered stent 120 that includes radially expanding thin-film mesh 100/110 of FIGS. 1A-C with slits 102 parallel to long axis 104 may require stent backbone 122 capable of more radial force such that the radial force can expand thin-film mesh 100/110 and open up slits 102 to diamond-shaped fenestrations 112. Thin-film covered stent 120 that includes longitudinally expanding thin-film mesh 100/110 of FIGS. 2A-C advantageously requires less radial force for stent backbone 122 to expand thin-film mesh 100/110 because thin-film mesh 100/110 is expanded before assembling on stent backbone 122. As thin-film mesh 100 of FIG. 2A is fabricated with a width (length along axis 206) that remains approximately equal after it is longitudinally expanded, thin-film mesh 110 of FIGS. 2B-C may bunch when crimpled in the catheter and may further provide radial force of its own to return to its non-crimped state when deployed, further reducing the radial force needed by stent backbone 122. Thus, as thin-film covered stent 120 utilizing thin-film mesh 100/110 of FIGS. 2A-C requires stent backbone 122 with less radial force to expand when deployed, stent backbone 122 may include less material such that a smaller delivery catheter may be used to deploy thin-film covered stent 120.

FIG. 4C is a diagrammatic cross-sectional view of a blood vessel 132 in which thin-film covered stent 120 with a variable porosity is inserted. Thin-film mesh 100 may be fabricated with a variable slit length along axis 104/204 such that it has a region with a higher slit density (e.g., slits with shorter slit length 114) and a region with a lower slit density (e.g., slits with longer slit length 114). The region with a higher slit density may be wider along axis 106/206 to account for less expansion along axis 106/206 than the region with lower slit density.

The region with the higher slit density results in a high pore density region 110a and the region with the lower slit density results in a low pore density region 110b. Advantageously, a higher pore density and higher percent metal coverage may be achieved at aneurysm neck 138 by placing high pore density region 110a at aneurysm neck 138, thereby reducing blood flow from flowing into the aneurysm and promote faster healing and more robust scaffold for parent artery reconstruction and endothelialization. Further, a low pore density and low percent metal coverage may be achieved at nearby branch vessels 136 by placing low pore density region 110b at regions other than aneurysm neck 138, thereby facilitating vessel healing while allowing better blood flow through branch arteries and, thus, making the device safer for patients. In some embodiments, thin-film covered stent 120 may include one or more radiopaque markers (e.g., gold markers) that delineate the transition zone between region 110a and region 110b. In other embodiments, the variation in pore density may be gradual such that there is no transition zone, in which case radiopaque markers may be positioned relative to an area having a higher pore density.

In some embodiments, thin-film mesh 110 includes high pore density region 110a in the middle along axis 104/204 and low pore density regions 110b flanking both sides of high pore density region 110a as shown in FIG. 4C. In other embodiments, thin-film mesh 110 includes high pore density region 110a on one side and a low pore density region on the other side along axis 104/204. In further embodiments, thin-film mesh 110 may only include high pore density region 110a that is placed over a defined portion of stent backbone 122 (e.g., in the middle or on one side) and forego low pore density region 110b altogether.

Figure 5:
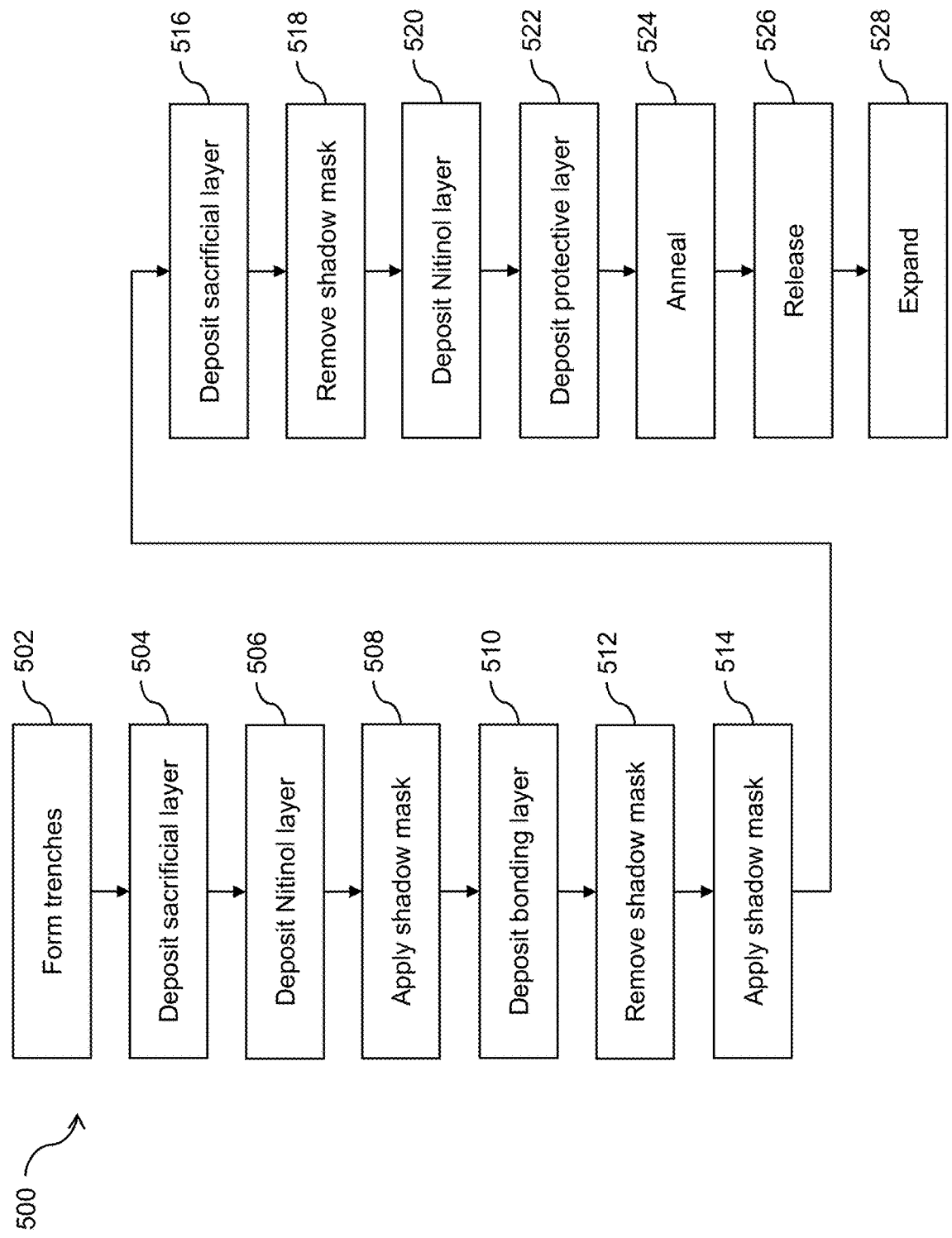
FIG. 5 is a flow diagram of a process to fabricate a thin-film mesh for a thin-film device according to an embodiment.
Figure 6E:
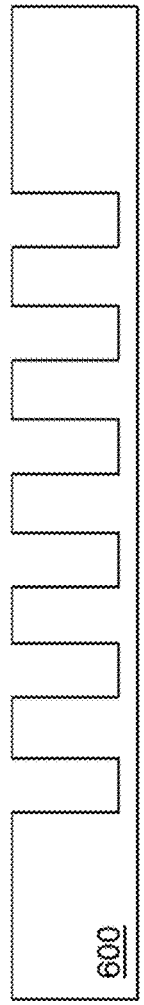
FIGS. 6A-6Q are diagrammatic cross-sectional views of layers being formed on a wafer to fabricate a thin-film mesh according to an embodiment.
Figure 7C:
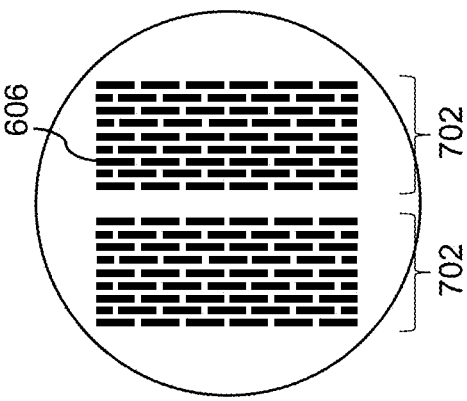
FIGS. 7A-7H are diagrammatic top plan views of layers being formed on a wafer to fabricate a thin-film mesh according to an embodiment.
Figure 7B:
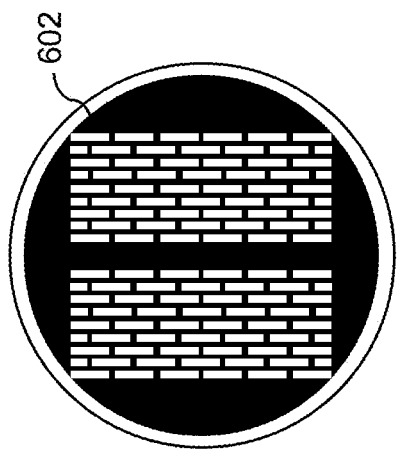
Figure 7A:
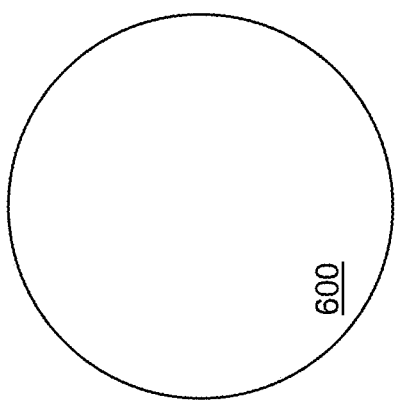

FIG. 5 is a flow diagram of a process 500 to fabricate a thin-film mesh, such as thin-film mesh 100/110 of FIGS. 1A-C or FIGS. 2A-C, for a thin-film device, such as thin-film covered stent 120 of FIG. 3. At block 502, trenches are formed on a wafer 600 (e.g., a silicon wafer or other wafer) as shown in FIGS. 6A-6E and 7A-7C. FIGS. 6A and 7A show wafer 600, which may have an oxide layer with a thickness of between 500 nm and 1 μm on top. A photoresist 602 is spun coated on wafer 600 as shown in FIG. 6B. By patterning and developing photoresist 602 using photolithography, a pattern of exposed areas 604 is formed as shown in FIG. 6C and FIG. 7B. The pattern of exposed areas 604 is available for etching. Deep reactive ion etching (DRIE) is performed to form trenches 606 that are at least 15 μm deep (e.g., between 25 μm and 200 μm deep) as shown in FIG. 6D. Photoresist 602 is removed and wafer 600 is cleaned, resulting in etched wafer 600 with trenches 606 as shown in FIG. 6E and FIG. 7C. Trenches 606 may form a micropattern that provide a template for thin-film mesh 100. The resolution of the micropattern using the DRIE process may be approximately 1 μm. Although two micropatterns 702 for two thin-film meshes are shown in FIG. 7C, wafer 600 may include more micropatterns.

Figure 6F:
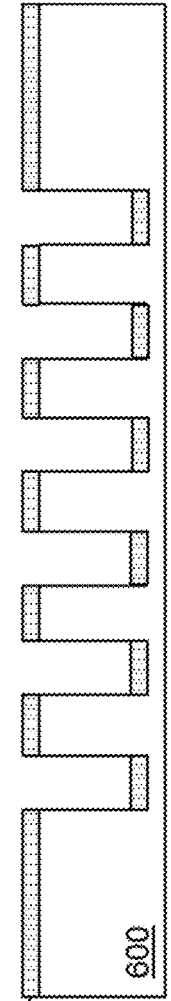

At block 504, a sacrificial layer 608 (e.g., a chrome sacrificial layer or a copper sacrificial layer), also referred to as a lift-off layer, is deposited as shown in FIG. 6F. Sacrificial layer 608 may be deposited by sputter deposition or evaporation deposition such as electron beam physical vapor deposition (EBPVD). Sacrificial layer 608 may have a thickness of, for example, 1 micron or less (e.g., approximately 500 nm).

Figure 6G:
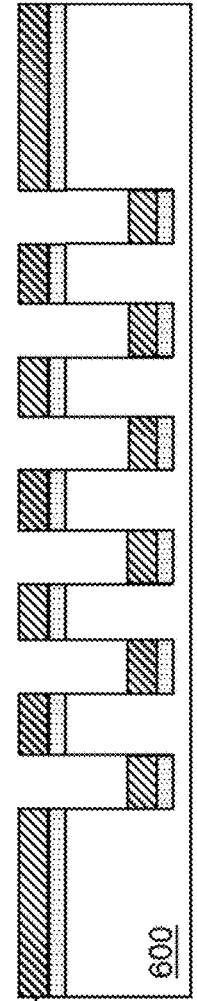
Figure 7E:
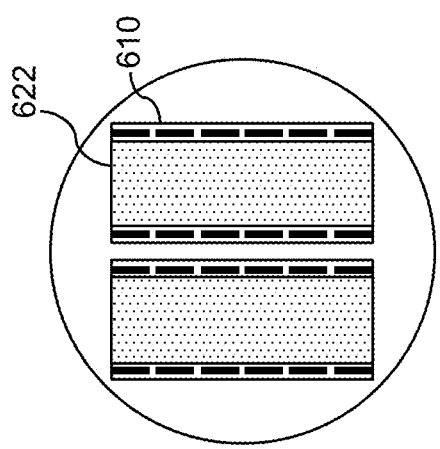
Figure 7D:
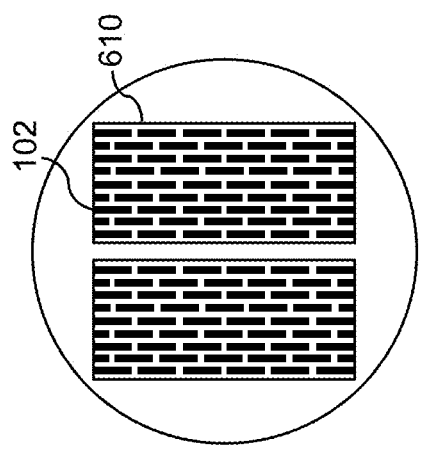

At block 506, a Nitinol layer 610 is deposited as shown in FIG. 6G and FIG. 7D. Nitinol layer 610 may have a thickness of, for example, between 1 micron and 20 microns (e.g., approximately 5 microns). As sputtered Nitinol at regions corresponding to trenches 606 fall to the bottom of trenches 606, trenches 606 of wafer 600 are duplicated on Nitinol layer 610 as corresponding fenestrations (e.g., closed fenestrations) such as slits 102 of thin-film mesh 100 as shown in FIG. 1A or FIG. 2A. The resulting pattern of fenestrations may also be denoted as a fiche in that the fenestrations are in closed form prior to an expansion of thin-film mesh 100. Just like a microfiche, each fiche or pattern of fenestrations effectively codes for the resulting fenestrations when thin-film mesh 100 is expanded to fully open up the fenestrations.

Figure 6H:
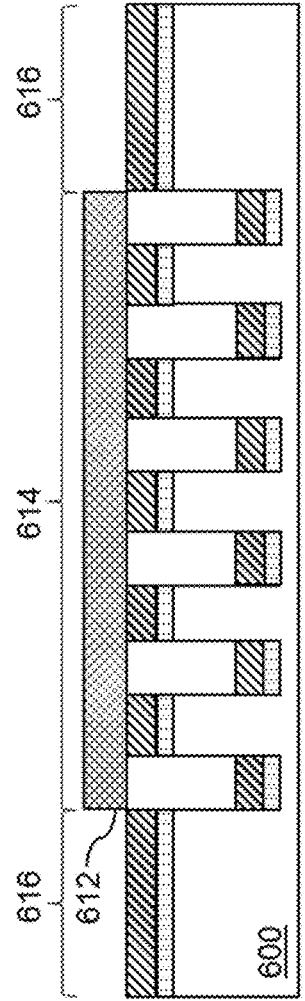

At block 508, a shadow mask 612 is applied as shown in FIG. 6H. Shadow mask 612 is applied to mesh region 614 and exposes seam regions 616 for deposition of a bonding layer 618.

Figure 6I:
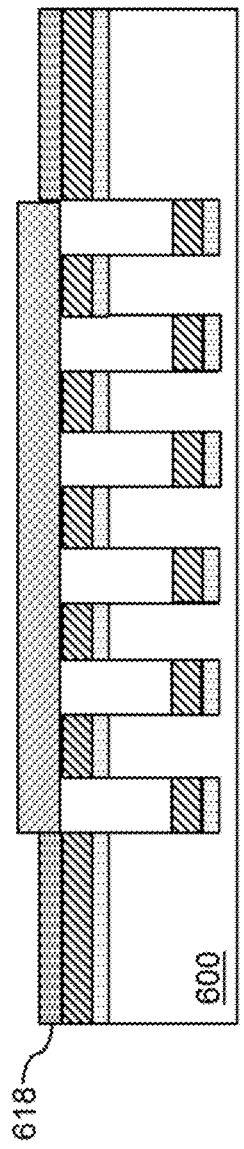

At block 510, bonding layer 618 (e.g., an aluminum bonding layer) is deposited as shown in FIG. 6I. Bonding layer 618 may have a thickness of, for example, 1 micron or less (e.g., approximately 500 nm).

Figure 6J:
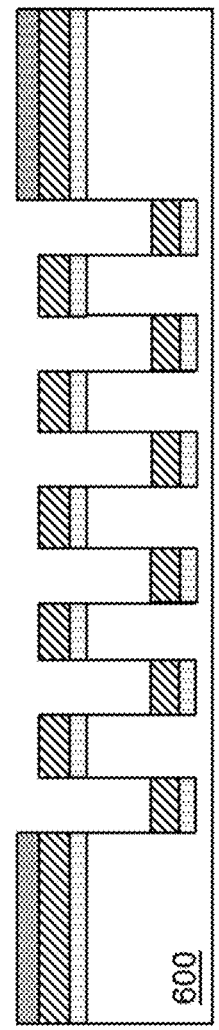

At block 512, shadow mask 612 is removed as shown in FIG. 6J.

Figure 6K:
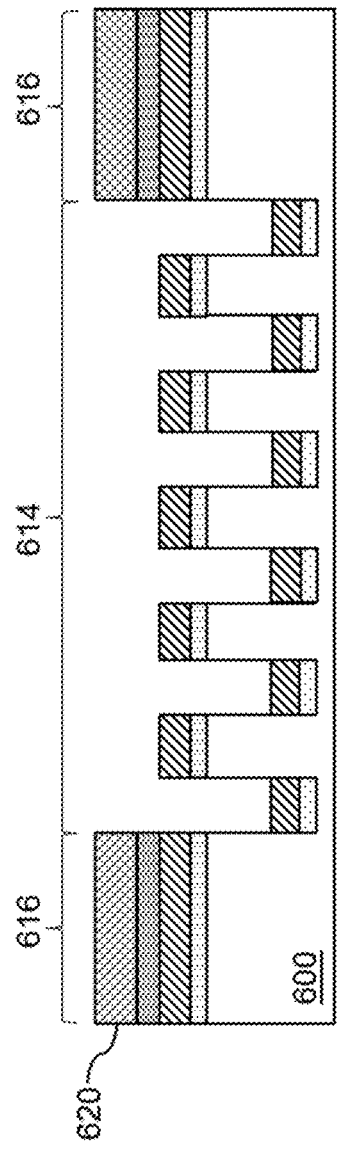

At block 514, a shadow mask 620 is applied as shown in FIG. 6K. Shadow mask 620 is applied to seam regions 616 and exposes mesh region 614 for deposition of a sacrificial layer 622.

Figure 6L:
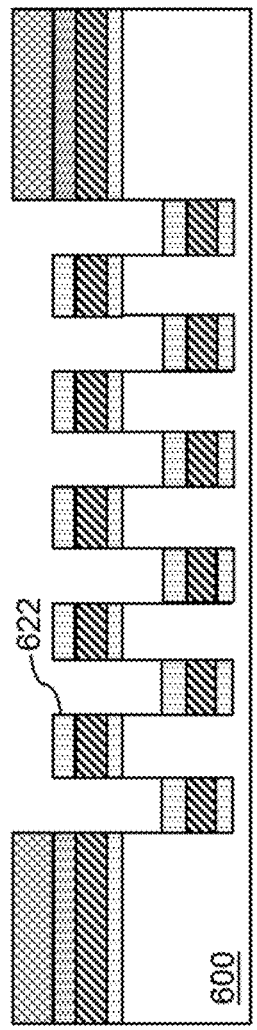

At block 516, sacrificial layer 622 (e.g., a chrome sacrificial layer) is deposited as shown in FIG. 6L and FIG. 7E. Sacrificial layer 622 may have a thickness of, for example, 1 micron or less (e.g., approximately 500 nm).

Figure 6M:
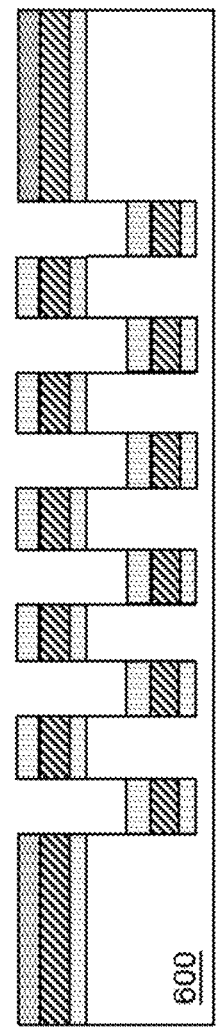

At block 518, shadow mask 620 is removed as shown in FIG. 6M.

Figure 6N:
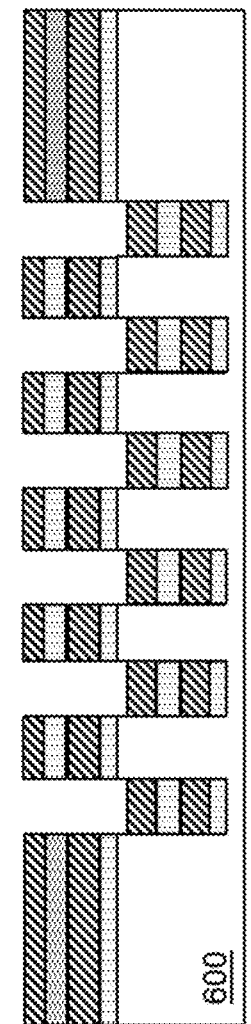
Figure 7G:
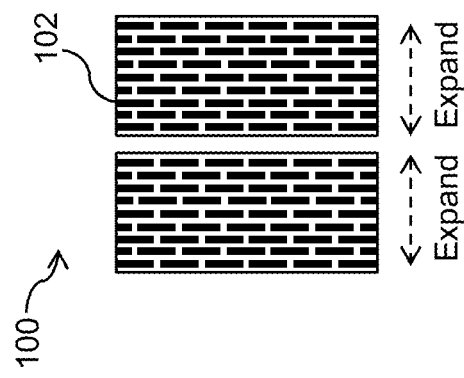
Figure 7F:
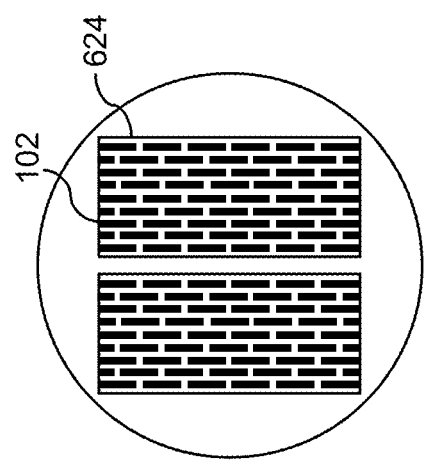

At block 520, a Nitinol layer 624 is deposited as shown in FIG. 6N and FIG. 7F. Nitinol layer 624 may have a thickness of, for example, between 1 micron and 50 microns (e.g., approximately 5 microns). Similarly to block 506, as sputtered Nitinol at regions corresponding to trenches 606 fall to the bottom of trenches 606, trenches 606 of wafer 600 are duplicated on Nitinol layer 624 as corresponding fenestrations (e.g., closed fenestrations) such as slits 102 of thin-film mesh 100 as shown in FIG. 1A or FIG. 2A.

Figure 6O:
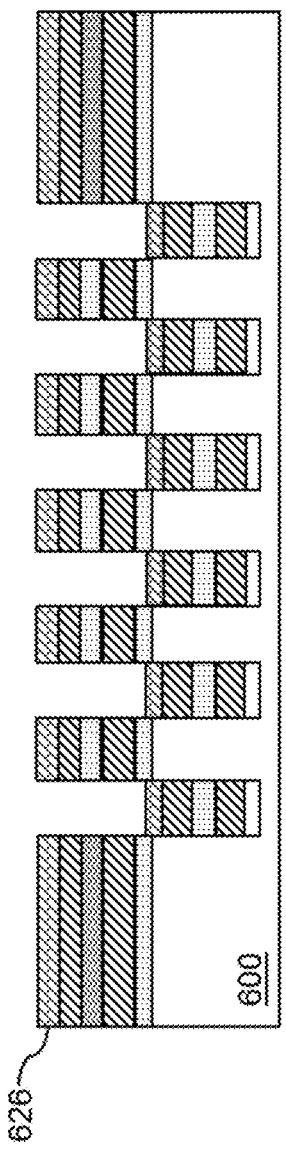

At block 522, a protective layer 626 (e.g., a protective chrome layer) is deposited as shown in FIG. 6O. Protective layer 626 may have a thickness of, for example, 1 micron or less (e.g., approximately 500 nm).

Figure 6P:
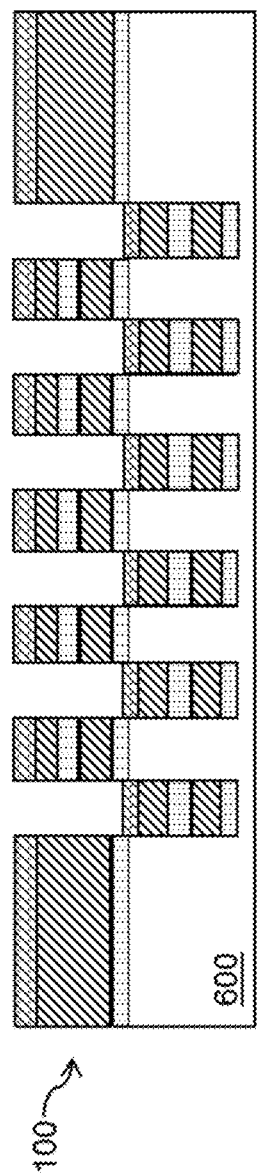

At block 524, Nitinol layers 610, 624 and bonding layer 618 are annealed to form thin-film mesh 100 as shown in FIG. 6P. Wafer 600 with Nitinol layers 610, 624 and bonding layer 614 may be annealed at a high temperature (e.g., approximately 675° C. for approximately 10 minutes) to melt bonding layer 618 and crystalize amorphous Nitinol layers 610, 624. Nitinol layer 610 and Nitinol layer 624 are fused in inseam region 616.

Figure 6Q:
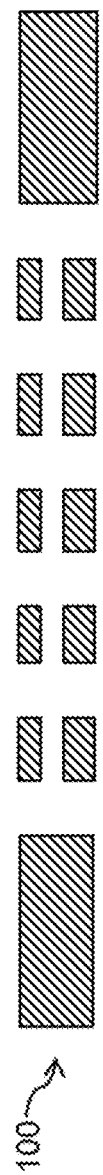

At block 526, thin-film mesh 100 is released as shown in FIG. 6Q and FIG. 7G. Annealed wafer 600 may be placed in chrome etchant (e.g., for approximately 1 hour) to release thin-film mesh 100 from top of wafer 600.

Figure 7H:
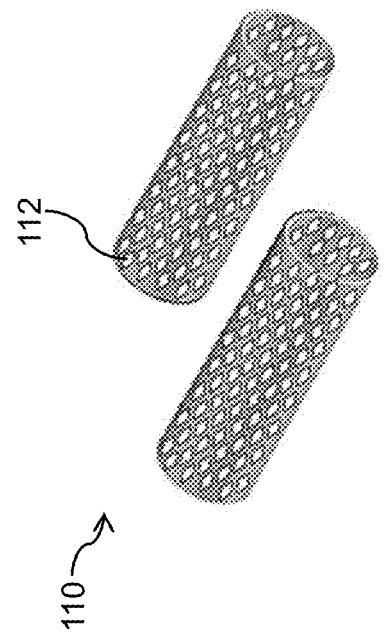

At block 528, thin-film mesh 100 is expanded as shown in FIG. 7H to form a three-dimensional cylindrical tube with fenestrations 112 that have been opened up.

Figure 8B:
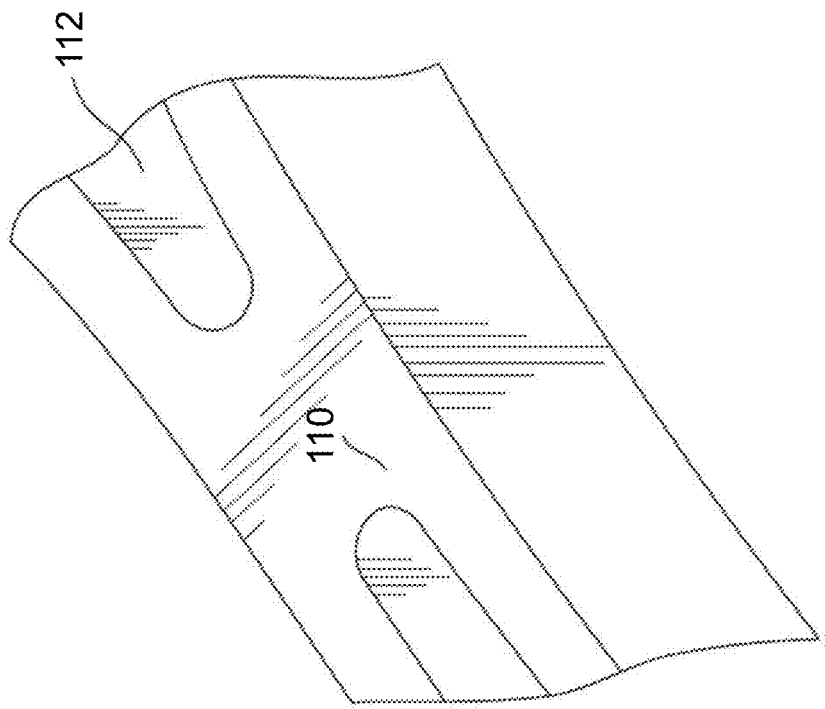
FIGS. 8A-8B are diagrammatic close-up views of a thin-film mesh according to an embodiment.
Figure 8A:
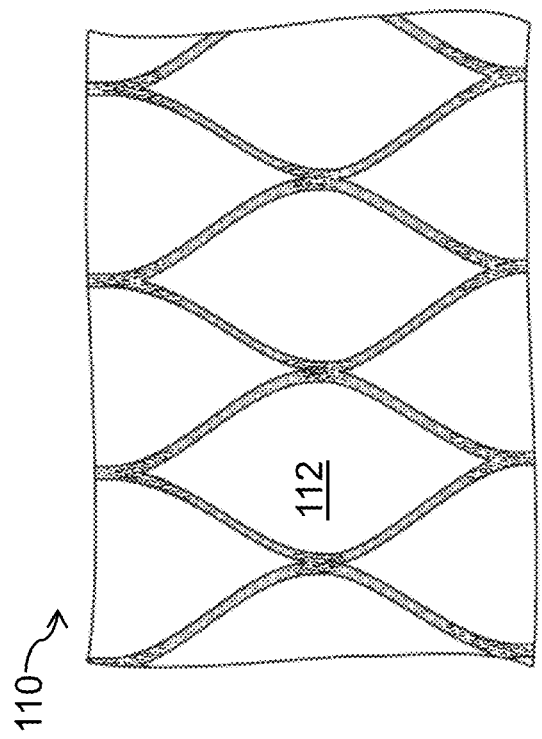

FIG. 8A is a diagrammatic close-up plan view of a portion of thin-film mesh 110 in FIGS. 1B-C or FIGS. 2B-C. Thin-film mesh 110 may have diamond-shaped pores 112 fabricated as slits 102 having slit length 114 of between 50 μm and 300 μm. Thin-film mesh 110 may have a pore density of between 70 pores/mm$^2$ and 1075 pores/mm$^2$, and a percent metal coverage of between 14% and 66%.

FIG. 8B is a diagrammatic close-up perspective view of thin-film mesh 110 in FIGS. 1B-C or FIGS. 2B-C. Conventional flow diverter stents made with wire meshes are not flat where the wires intertwine. In contrast, because thin-film mesh 110 is made with a layer of material such as Nitinol and expanded, there is no intertwining of wires. Thus, thin-film mesh is flat all around pores 112, which is advantageous for promoting rapid deposition of fibrin and cell growth (e.g., endothelialization).

Figure 9B:
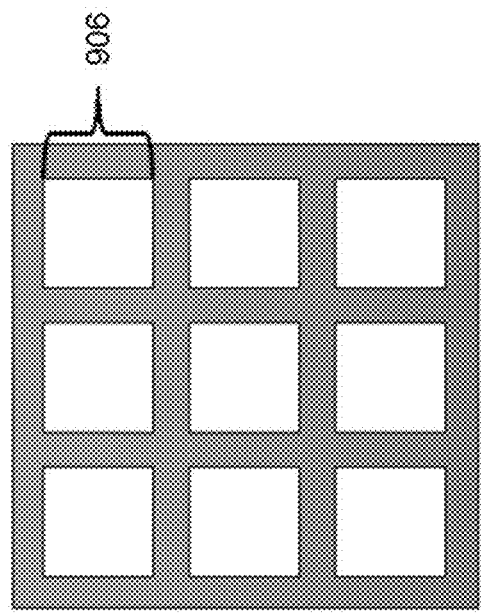
FIGS. 9A-9B illustrate thin-film mesh fenestration designs that have the same porosity but different pore densities according to one or more embodiments.
Figure 9A:
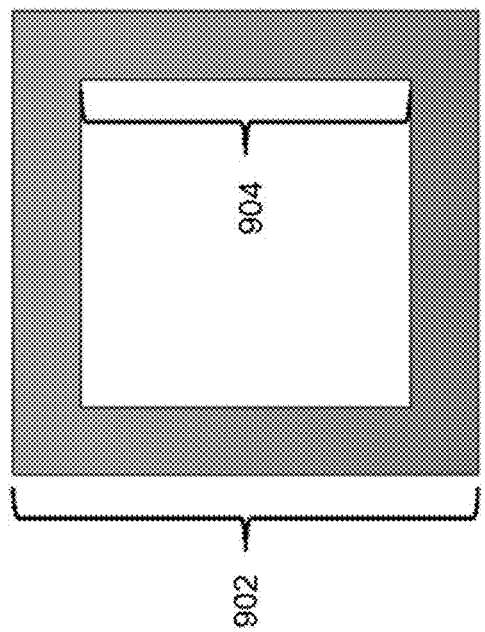

FIGS. 9A-B illustrate thin-film mesh fenestration designs that have the same porosity but different pore densities. The primary characteristics that determine the degree of flow diversion are percent metal coverage (PMC) and pore density, where higher percent metal coverage and higher pore density yield an increased flow diverting effect. Percent metal coverage is the fraction of the area of metal over the total area. Porosity is the fraction of the open area over the total area. Accordingly, for expanded thin-film mesh 110, the porosity and percent metal coverage of thin-film mesh 110 add up to 1, or 100%. Similarly, for thin-film covered stent 120, the porosity of thin-film covered stent, the percent metal coverage of thin-film mesh 110, and the percent metal coverage of stent backbone 122 add up to 1, or 100%.

The surface shown in FIG. 9A has a length 902 of 1 mm and a length 904 of 0.71 mm, such that the surface has a porosity of 50%, a pore density of 1 pore/mm$^2$, and a total edge length of 2.84 mm. The surface shown in FIG. 9B has a length 902 of 1 mm and a length 906 of 0.24 mm, such that the surface has a porosity of 50%, a pore density of 9 pore/mm$^2$, and a total edge length of 8.64 mm. Even though the pore designs of FIG. 9A and FIG. 9B have the same porosity of 50%, the design in FIG. 9A has a pore density of 1 pore/area while the design in FIG. 9B has a pore density of 9 pores/area. For flow diverter stents, two flow diverter stents having similar porosity and percent metal coverage may have drastically different efficacy due to different pore density. For example, thin-film covered stents 120 with a percent metal coverage of 10-15% and 50-100 pores/mm$^2$ are more effective compared to a conventional flow diverter stent having a percent metal coverage of 35% and 14 pores/mm$^2$. Thin-film covered stents 120 with a percent metal coverage of 25-35% and 150-250 pores/mm$^2$ are even more effective compared to conventional flow diverter stents having a percent metal coverage of 35% and 14 pores/mm$^2$ because the increased pore density provides more friction per unit area and provides a surface for fibrin deposition and cell growth (e.g., endothelialization).

Figure 10A:
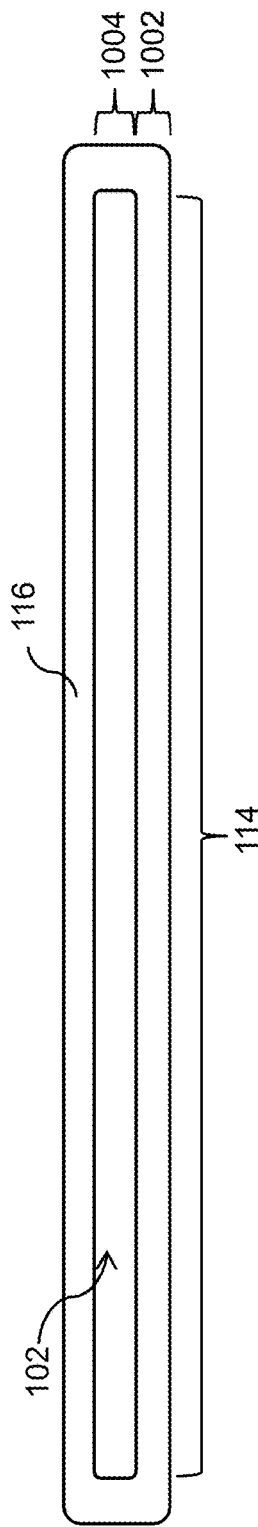
FIGS. 10A-10B illustrate a fenestration of a thin-film mesh before and after expansion according to an embodiment.
Figure 10B:
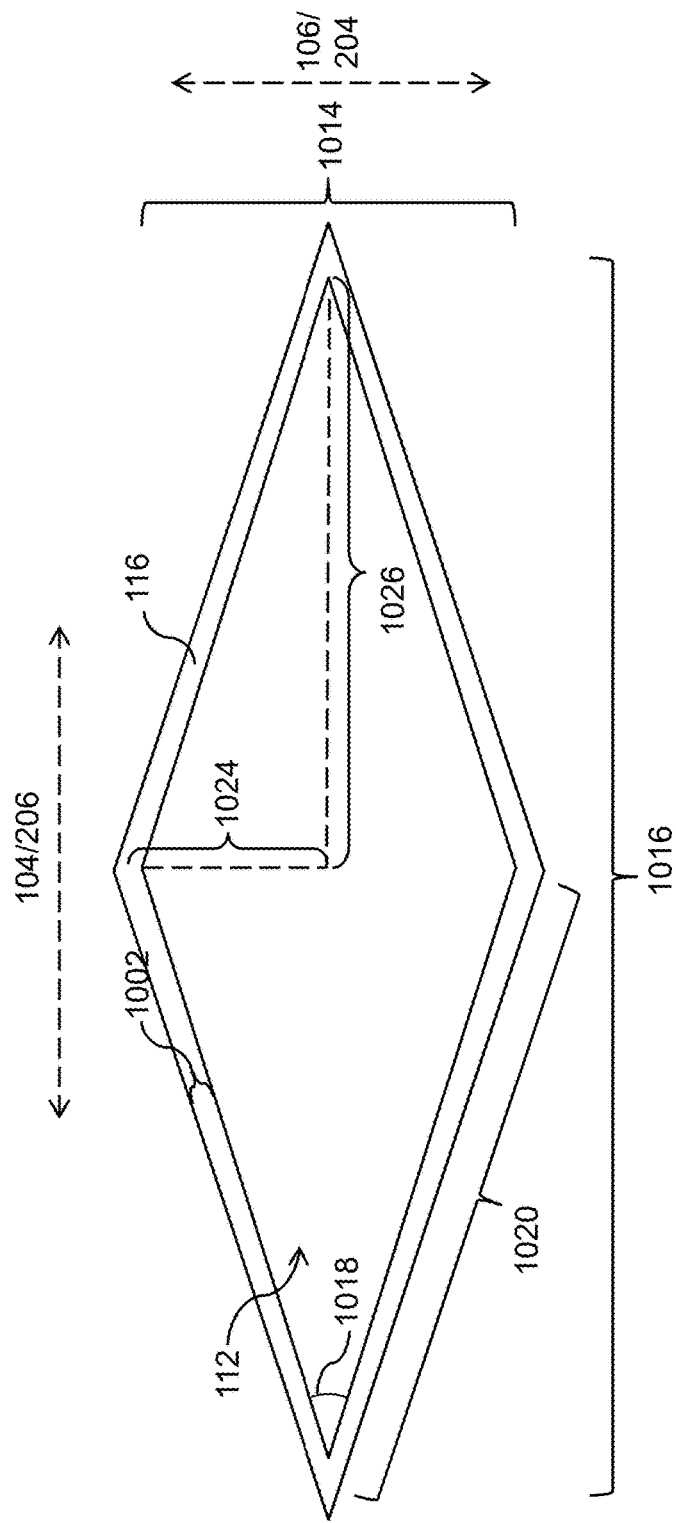

FIGS. 10A-B illustrate fenestration 112 of thin-film mesh 100 before and after expansion. FIG. 10A illustrates slit 102 (e.g., a closed fenestration) and a surrounding struts 116 of thin-film mesh 110 before expansion. Surrounding struts 116 may have a strut width 1002, which may be between 1 and 25 μm. Slit 102 may have a slit width 1004 and a slit length 114. One half of slit width may be referred to as $Y_1$, and one half of slit length 114 may be referred to as $X_1$.

FIG. 10B illustrates pore 112 (e.g., an open fenestration) and surrounding strut 116 of thin-film mesh 110 after expansion. Surrounding strut 116 may have a strut width 1002, which may be between 1 and 25 μm. Diamond-shaped pore 112 may have a short diagonal length 1014 along short diagonal axis such as axis 106 of FIGS. 1A-C or axis 204 of FIGS. 2A-C, a long diagonal length 1016 along long diagonal axis such as axis 104 of FIGS. 1A-C or axis 206 of FIGS. 2A-C, and a side length 1020. Diamond-shaped pore 112 may further have a strut angle θ 1018. In some embodiments, strut angle θ 1018 may be between 30 and 90 degrees. Length 1024, which is one half of short diagonal length 1014, may be referred to as $Y_2$, and length 1026, which is one half of long diagonal axis 1016 may be referred to as $X_2$.

As side length 1020 is equal or approximately equal (e.g., slightly larger due to elongation of Nitinol thin-film mesh) to half of slit length 114 in FIG. 10A (given that pore 112 open up from slit 102), side length 1020 may equal or be approximated as $X_1$. The lengths $X_1$, $X_2$, and $Y_2$, and strut angle θ may be related by the following equations:

$$\cos\frac{\theta}{2} = \frac{X_2}{X_1}$$

$$\sin\frac{\theta}{2} = \frac{Y_2}{X_1}$$

Accordingly, a percentage change in X and a percentage change in Y may be calculated. For example, if slit length 114 is 150 μm and slit width 1004 is 10 μm, and strut angle θ 1018 is 45°, then: $X_1$=75 μm, $Y_1$=5 μm, $X_2$=69.3 μm, $Y_2$=28.7 μm. The percent change in X is small, −7.6%, when compared to the percent change in Y, 474%.

For thin-film mesh 100 of FIG. 1A, the longitudinal length of thin-film mesh 100 (length along axis 104) will decrease by 7.6% when expanded along axis 106 to form thin-film mesh 110 of FIGS. 1B-C. For thin-film mesh 100 of FIG. 2A, the width of thin-film mesh 100 (length along axis 206) will decrease by 7.6% when expanded along axis 204 to form thin-film mesh 110 of FIGS. 2B-C. The circumference of cylindrical thin-film mesh 110 of FIGS. 2B-C may be 7.6% smaller than twice the width of thin-film mesh 100 in FIG. 2A taking into account the two layers of thin-film mesh 100.

Further, other features of diamond-shaped pores 112 may be determined by the following equations:

$$\text{Pore area} = 2X_2Y_2$$

$$\text{Pore area with strut metal} = 2(X_2 + W)(Y_2 + W)$$

$$\text{Pore density} = \frac{1}{2(X_2 + W)(Y_2 + W)}$$

$$\text{Percent metal coverage} = 1 - \frac{2X_2Y_2}{2(X_2 + W)(Y_2 + W)}.$$

For example, if slit length 114 is 150 μm, slit width 1004 is 10 μm, strut width 1002 is 8 μm, and strut angle θ 1018 is 30°, then: $X_1$=75 μm, $Y_1$=5 μm, $X_2$=72 μm $Y_2$=19 μm, pore area=0.0027 mm$^2$, pore area with strut metal=0.0043 mm$^2$, pore density=230 pores/mm$^2$, and percent metal coverage=37%.

Figure 11B:
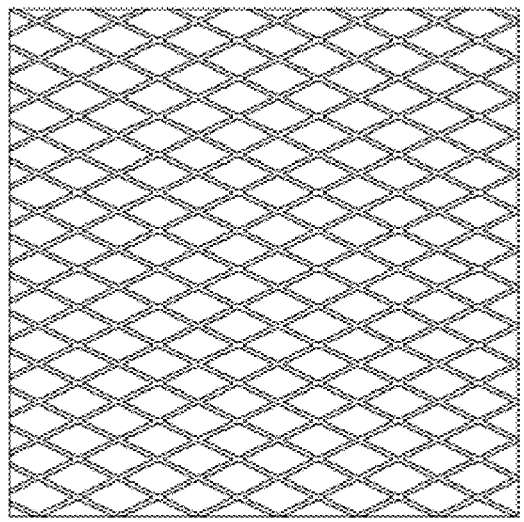
FIG. 11B is a diagrammatic top plan view of a portion of a thin-film mesh of another thin-film covered stent ("Device 2") according to an embodiment.
Figure 11A:
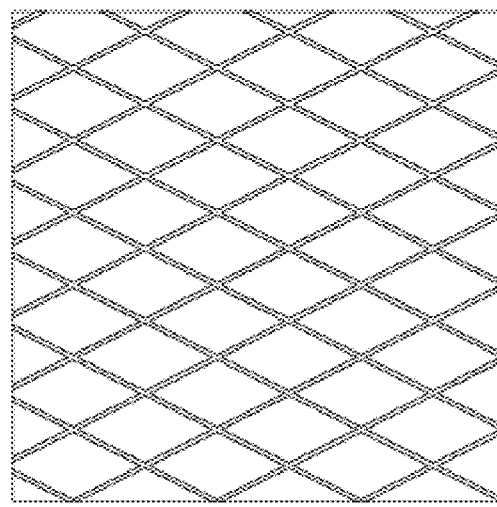
FIG. 11A is a diagrammatic top plan view of a portion of a thin-film mesh of a thin-film covered stent ("Device 1") according to an embodiment.

FIG. 11A is a diagrammatic top plan view of a portion of a thin-film mesh 110 of a thin-film covered stent ("Device 1"), such as thin-film covered stent 120 of FIG. 3. Device 1 is an illustrative example of thin-film covered stent 120 with thin-film mesh 110 fabricated with slit length 114 of between 225 μm and 400 μm. Thin-film mesh 110 of Device 1 has a slit length 114 of 300 μm as fabricated. Upon expansion, thin-film mesh 110 of Device 1 may have a pore density of between 38 and 70 pores/mm$^2$, assuming a strut angle between 30 and 90 degrees. Device 1 may have a percent metal coverage of between 14% and 21%, and an edge density of between 23 mm of edge per mm$^2$ of surface area and 42 mm of edge per mm$^2$ of surface area.

FIG. 11B is a diagrammatic top plan view of a portion of a thin-film mesh 110 of another thin-film covered stent ("Device 2"), such as thin-film covered stent 120 of FIG. 3. Device 2 is an illustrative example of thin-film covered stent 120 with thin-film mesh 110 fabricated with slit length 114 of between 50 μm and 200 μm. Thin-film mesh 110 of Device 2 has a slit length 114 of 150 μm as fabricated. Upon expansion, Device 2 may have a pore density of between 134 and 227 pores/mm$^2$, assuming a strut angle between 30 and 90 degrees. Device 2 may have a percent metal coverage of between 24% and 36%, and an edge density of between 40 mm of edge per mm² of surface area and 68 mm of edge per mm² of surface area. Device 2 with a greater pore density advantageously facilitates more rapid and optimal healing of tissue defects such as aneurysms compared to Device 1.

Figure 12A:
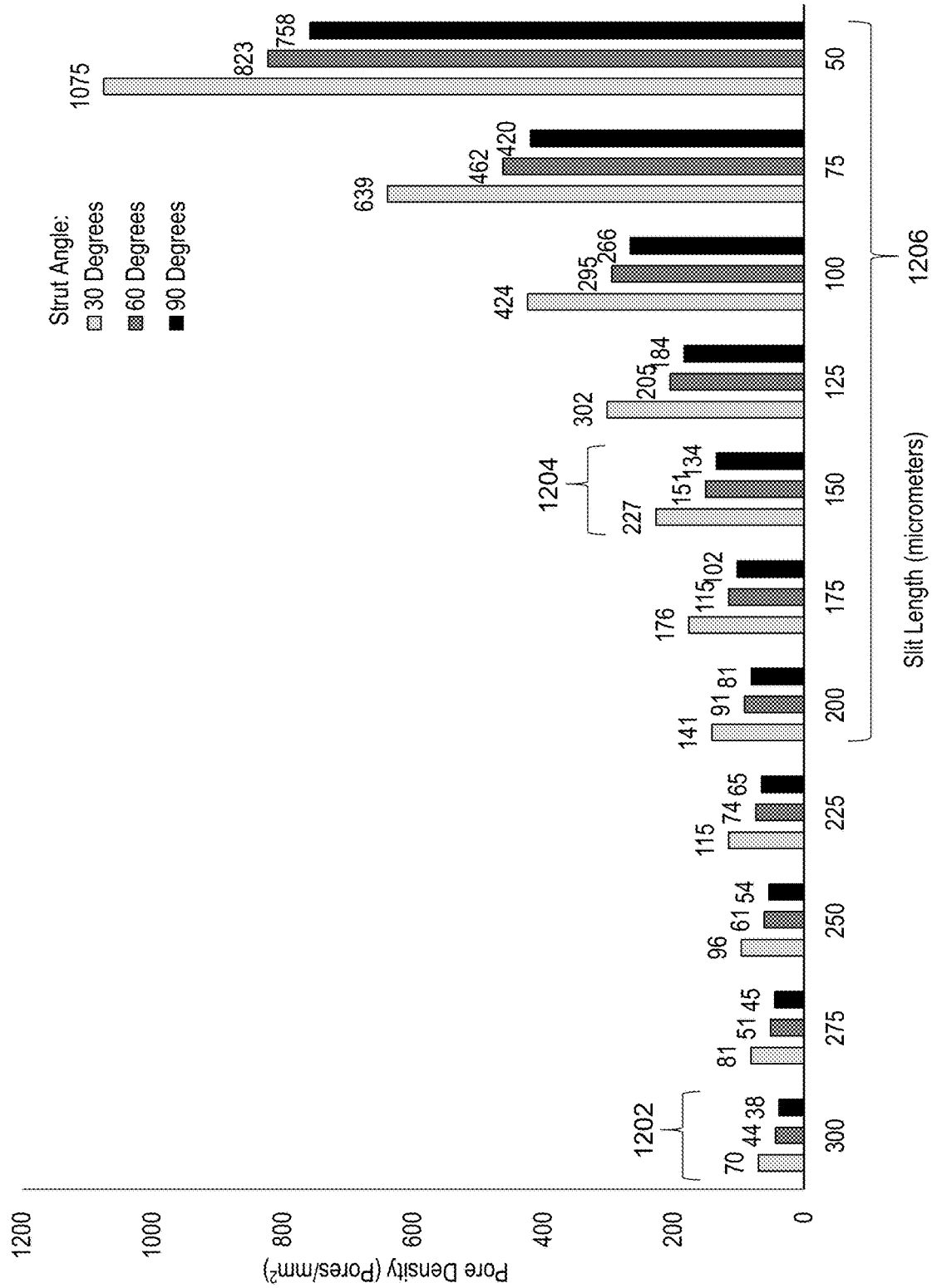
FIGS. 12A-12C are graphs characterizing thin-film meshes when one or more features are varied according to one or more embodiments.
Figure 12B:
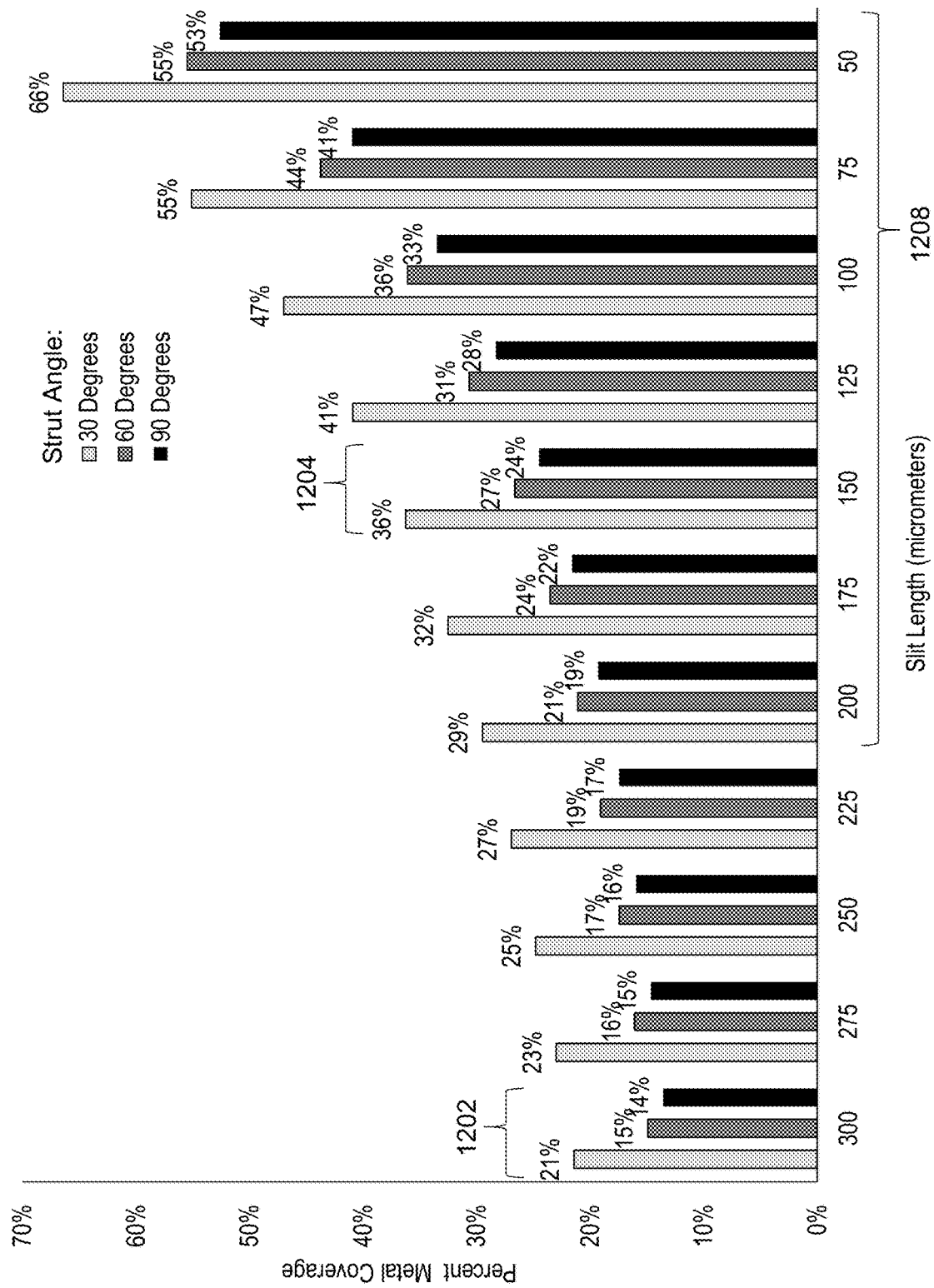
Figure 12C:
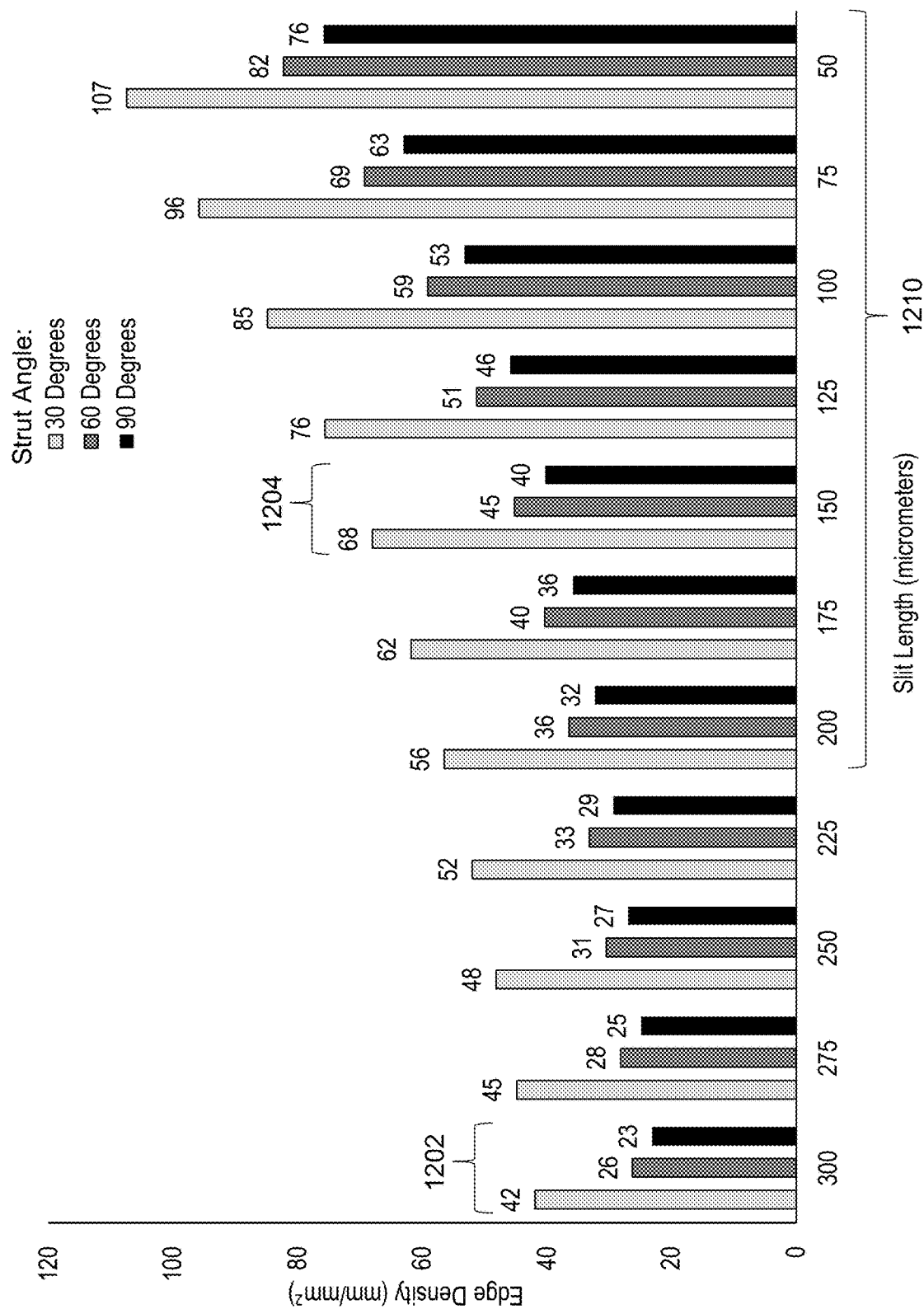

FIGS. 12A-C are graphs characterizing thin-film meshes 110 when one or more physical characteristics are varied. FIG. 12A shows a graph of pore density vs. slit length 114, assuming an 8 µm strut width. FIG. 12B shows a graph of percent metal coverage vs. slit length 114, assuming an 8 µm strut width. FIG. 12C shows a graph of edge density vs. slit length 114, assuming an 8 µm strut width. The ranges of physical characteristics 1202 of thin-film mesh 110 used in Device 1, The ranges of physical characteristics 1204 of thin-film mesh 110 used in Device 2, and the ranges of physical characteristics 1206, 1208, and 1210 that provide thin-film mesh 110 with advantageous properties including rapid fibrin deposition and cell growth (e.g., endothelialization) are shown in FIGS. 12A-C.

Device 1 and Device 2 were used in model aneurysms created in animals. Eight model arterial aneurysms were created in rabbits and treated with Device 1. Six model arterial aneurysms were created in rabbits and treated with Device 2. The animals were then sacrificed after 4 weeks and the degree of aneurysm neck healing was examined by removing the arterial vessel segments containing the devices and the model aneurysms for pathological analysis. For the pathological analysis, the arterial vessels were cut along their long axis generating two approximately equal halves, with one half containing the model aneurysm. The sections with the model aneurysm were analyzed with light microscopy and CD31 immunostaining for differences in tissue in-growth. The sections of the devices and micromesh covering the aneurysm neck region was the primary area of interest.

Figure 13B:
FIGS. 13A-13B are images of Device 1 explanted 4 weeks after treating an in vivo model aneurysm.
Figure 13D:
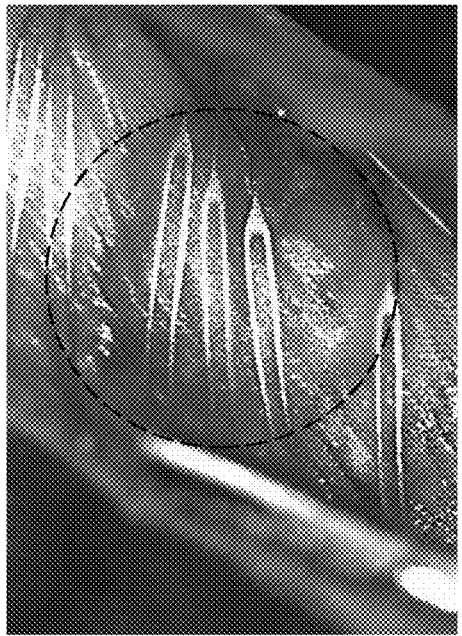
FIGS. 13C-13D are images of Device 2 explanted 4 weeks after treating an in vivo model aneurysm.
Figure 13A:
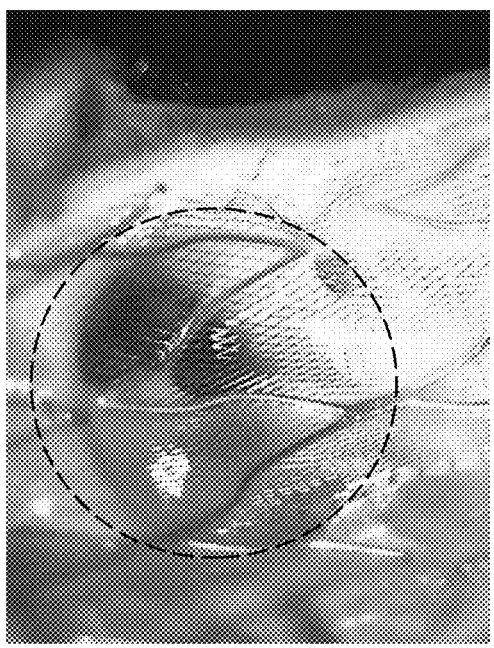
Figure 13C:
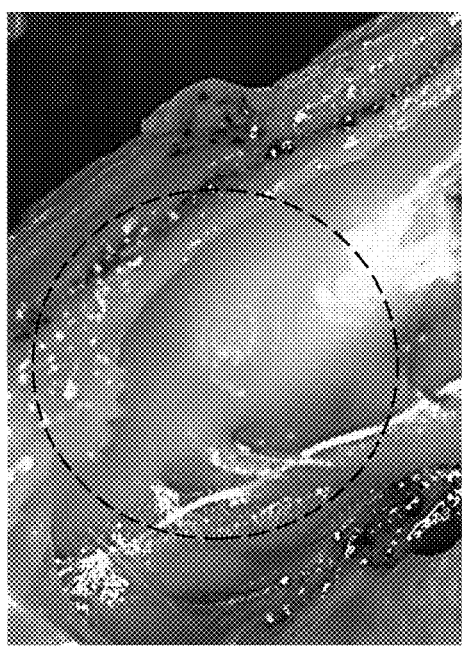

Results of the light microscopy analysis are shown in FIGS. 13A-D. FIGS. 13A-B are images showing results from Device 1 (low pore density micromesh) and FIGS. 13C-D are images showing results from Device 2 (high pore density micromesh). As shown in FIGS. 13A-B, it can be seen that the aneurysms treated with Device 1 failed to heal completely. Large portions of the aneurysm neck region still exposed, and thin-film mesh 110 is clearly visible. In contrast, as shown in FIGS. 13C-D, the aneurysms treated with Device 2 demonstrated a robust tissue in-growth. The aneurysm neck region is almost indistinguishable from the surrounding vessel and thin-film mesh 110 has been fully covered with tissue. These findings indicate that thin-film mesh 110 with high pore density is a superior scaffold for repairing tissue defects, and encouraging cell growth in general. Such a scaffold has a wide array of potential applications.

It can also be appreciated from these images that the cellular growth tends to start at the edges of the aneurysm neck region and grow towards the center. Although a conventional stent may be covered with tissue and incorporated into vessel wall following successful placement at a small tissue defect, placement of conventional stent over a large tissue defect, such as an aneurysm neck, will typically not result in aneurysm occlusion or re-growth of the vessel wall. Therefore, the microporous mesh-based stent, such as thin-film covered stent 120 of FIG. 3, is a unique device that facilitates tissue regrowth and healing of larger tissue defects. These results also stand in contrast to those achieved clinically with conventional flow-diverting stents that are specifically designed to treat aneurysms. Conventional flow diverting stents are tubular structures manufactured by braiding a series of fine wires. Recently published clinical reports indicate that while these devices can be effective at occluding aneurysms, they typically do so on a very delayed time scale following placement (i.e. on the order of months to years) and they often fail to endothelialize, which can lead to severe clinical complications including stroke and death.

Figure 14B:
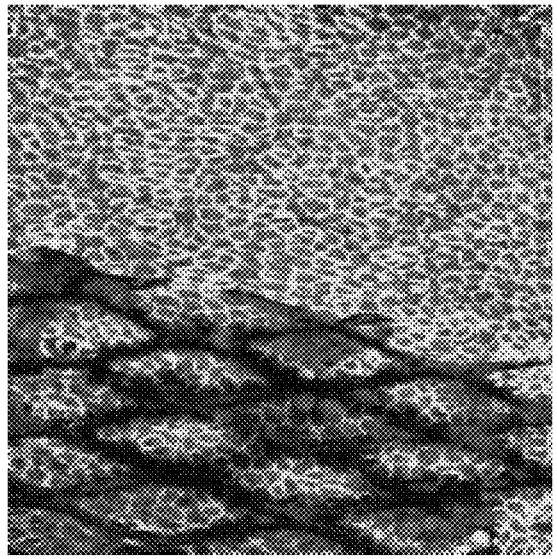
FIGS. 14A-14B are a CD31 immunohistochemistry images of Device 1 explanted 4 weeks after treating an in vivo model aneurysm.
Figure 14A:
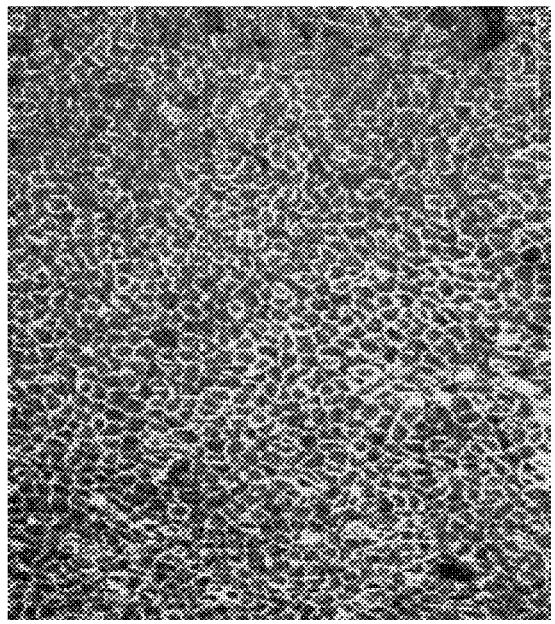

The results of CD31 immunostaining of Device 1 covering the aneurysm neck region are shown in FIGS. 14A-B. FIG. 14A is an image showing a confluent endothelial layer exhibiting the cobblestone morphology that is indicative of healthy endothelial growth. FIG. 14B is an image showing endothelial cells interacting with a partially-exposed high pore density thin-film mesh 110 of Device 1. These findings indicate the porous micromesh facilitates growth of a healthy endothelial layer, which is the desired outcome for implantable endovascular device, especially when treating a substantial tissue defect such as an aneurysm.

Embodiments described herein illustrate but do not limit the disclosure. It should also be understood that numerous modifications and variations are possible in accordance with the principles of the present disclosure. Accordingly, the scope of the disclosure is best defined only by the following claims.

What is claimed is:

1. A method comprising:
deep reactive ion etching a micropattern of trenches on a surface of a semiconductor substrate, the trenches corresponding to slits in a desired thin-film Nitinol mesh, wherein the etching of the micropattern of trenches comprises etching the micropattern of trenches such that the thin-film Nitinol mesh, when expanded, has pore densities of between 81 and 1075 pores per mm², and comprises a region of high pore density flanked by regions of low pore density, wherein radiopaque markers delineate transition zones between the regions;
depositing a lift-off layer on the grooved semiconductor substrate surface;
depositing a first Nitinol layer over the lift-off layer;
depositing a sacrificial layer over the first Nitinol layer leaving edges along the longitudinal axis exposed;
depositing a second Nitinol layer over the sacrificial layer;
etching the lift-off layer and the sacrificial layer to form the thin-film Nitinol mesh;
expanding the thin-film Nitinol mesh along the longitudinal axis to open the slits to corresponding pores, each pore having a long axis and a short axis; and
attaching the expanded thin-film Nitinol mesh to a stent backbone such that the long axis of the pores are perpendicular to a longitudinal axis of the stent backbone.

2. The method of claim 1, wherein the etching of the micropattern of trenches comprises etching the micropattern of trenches such that the thin-film Nitinol mesh, when expanded, has percent metal coverages of between 19 and 66%.

3. The method of claim 1, wherein the etching of the micropattern of trenches comprises etching the micropattern of trenches corresponding to slit lengths of between 50 and 250 micrometers.

4. The method of claim 1, wherein the depositing of the first thin-film Nitinol layer and the depositing of the second thin-film Nitinol layer comprise depositing Nitinol to a thickness of between 1 and 50 micrometers.

5. The method of claim 1, wherein the expanding of the thin-film Nitinol mesh forms the pores having a largest dimension of less than 250 micrometers, and wherein the attaching the expanded thin-film Nitinol mesh to the stent backbone forms a carotid stent configured to be deployed at a carotid artery.

6. The method of claim 1, further comprising coating the thin-film Nitinol mesh with a drug eluting polymer to reduce a rate of neointimal hyperplasia or increases biocompatibility or hemocompatibility of the thin-film Nitinol mesh.

* * * * *